(12) United States Patent
Amegadzie et al.

(10) Patent No.: US 7,659,250 B2
(45) Date of Patent: Feb. 9, 2010

(54) BMP-7 VARIANT COMPOSITIONS, METHODS AND USES

(75) Inventors: Bernard Amegadzie, Phoenixville, PA (US); Mark Cunningham, Kennett Square, PA (US); Haimanti Dorai, Exton, PA (US); Jeffrey Luo, Malvern, PA (US); Juliane Mills, Wallingford, PA (US); Bethany Swencki-Underwood, Chester Springs, PA (US)

(73) Assignee: Centocor, Inc., Malvern, PA (US)

( * ) Notice: Subject to any disclaimer, the term of this patent is extended or adjusted under 35 U.S.C. 154(b) by 0 days.

(21) Appl. No.: 11/760,146

(22) Filed: Jun. 8, 2007

(65) Prior Publication Data

US 2008/0032919 A1    Feb. 7, 2008

Related U.S. Application Data

(63) Continuation-in-part of application No. PCT/US2006/048730, filed on Dec. 20, 2006.

(60) Provisional application No. 60/752,969, filed on Dec. 22, 2005, provisional application No. 60/820,538, filed on Jul. 27, 2006.

(51) Int. Cl.
*A61K 38/16* (2006.01)
*A61K 38/17* (2006.01)
*A61K 38/18* (2006.01)
*C07K 14/00* (2006.01)
*C07K 14/435* (2006.01)
*C07K 14/46* (2006.01)
*C07K 14/465* (2006.01)
*C07K 14/47* (2006.01)
*C07K 14/475* (2006.01)
*C07K 14/51* (2006.01)

(52) U.S. Cl. .............. 514/12; 514/2; 514/7; 514/8; 530/350

(58) Field of Classification Search ............ None
See application file for complete search history.

(56) References Cited

U.S. PATENT DOCUMENTS

| | | | | |
|---|---|---|---|---|
| 5,194,596 | A | * | 3/1993 | Tischer et al. ............ 530/399 |
| 5,350,836 | A | * | 9/1994 | Kopchick et al. ........ 530/399 |
| 2002/0028453 | A1 | | 3/2002 | Keck et al. |
| 2005/0114037 | A1 | | 5/2005 | Desjarlais et al. |
| 2005/0255141 | A1 | | 11/2005 | Oppermann et al. |

FOREIGN PATENT DOCUMENTS

| | | | |
|---|---|---|---|
| WO | WO 94/03600 | A1 | 2/1994 |
| WO | WO 99/03887 | A1 | 1/1999 |
| WO | WO 99/37320 | A1 | 7/1999 |
| WO | WO 00/20591 | A2 | 4/2000 |
| WO | WO 00/20607 | * | 4/2000 |
| WO | WO 2005/097825 | A2 | 10/2005 |

OTHER PUBLICATIONS

Vukicevic et al., 1996, PNAS USA 93:9021-9026.*

(Continued)

*Primary Examiner*—Elizabeth C. Kremmerer
(74) *Attorney, Agent, or Firm*—Kirk Baumeister

(57) ABSTRACT

Human Bone Morphogenic Protein 7 (hBMP-7) variant peptide chains, nucleic acids encoding these peptide chains, and methods of making and using the foregoing are disclosed.

3 Claims, 5 Drawing Sheets

```
         10         20         30         40         50         60
MHVRSLRAAA PHSFVALWAP LFLLRSALAD FSLDNEVHSS FIHRRLRSQE RREMQREILS
         70         80         90        100        110        120
ILGLPHRPRP HLQGKHNSAP MFMLDLYNAM AVEEGGGPGG QGFSYPYKAV FSTQGPPLAS
        130        140        150        160        170        180
LQDSHFLTDA DMVMSFVNLV EHDKEFFHPR YHHREFRFDL SKIPEGEAVT AAEFRIYKDY
        190        200        210        220        230        240
IRERFDNETF RISVYQVLQE HLGRESDLFL LDSRTLWASE EGWLVFDITA TSNHWVVNPR
        250        260        270        280        290        300
HNLGLQLSVE TLDGQSINPK LAGLIGRHGP QNKQPFMVAF FKATEVHFRS IRSTGSKQRS
        310        320        330        340        350        360
QNRSKTPKNQ EALRMANVAE NSSSDQRQAC KKHELYVSFR DLGWQDWIIA PEGYAAYYCE
        370        380        390        400        410        420
GECAFPLNSY MNATNHAIVQ TLVHFINPET VPKPCCAPTQ LNAISVLYFD DSSNVILKKY
        430
RNMVVRACGC H
```

OTHER PUBLICATIONS

Massague, 1987, Cell 49:437-438.*
Benjamin et al., 1998, Development 125:1591-1598.*
Pilbeam et al., 1993, Bone 14:717-720.*
Skolnick et al., 2000, Trends in Biotech. 18:34-39.*
Bork, 2000, Genome Research 10:398-400.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Wells, 1990, Biochemistry 29:8509-8517.*
Ngo et al., 1994, The Protein Folding Problem and Tertiary Structure Prediction, Merz et al., eds., Birkhauser, Boston, pp. 492-495.*
Gregory, et al., "The prodomain of BMP-7 targets the BMP-7 complex to the extracellular matrix," Journal of Biological Chemistry, 280(30): 27970-27980(2005). GenBank Accession No. NP 001710 (Jun. 11, 2005).
Greenwald, et al., "The BMP7/ActRII Extracellular Domain Complex Provides New Insights into the Cooperative Nature of Receptor Assembly," Molecular Cell, 11: 605-617 (2003).
Griffith, et al., "Three-dimensional structure of recombinant human osteogenic protein 1: Structural paradigm for the transforming growth factor $\beta$ superfamily," Proceedings of the National Academy of Science USA, 93: 878-883 (1996).
Keller, et al., "Molecular recognition of BMP-2 and BMP receptor IA," Nature Structural & Molecular Biology, 11(5): 481-488 (2004).
Groppe, et al., "Structural basis of BMP signaling inhibition by the cystine knot protein Noggin," Nature, 420: 636-642 (2002).
Özkaynak, et al., "OP-1 cDNA encodes an osteogenic protein in the TGF-$\beta$ family," The EMBO Journal, 9(7): 2085-2093 (1990).
Saulo Klahr, "The bone morphogenetic proteins (BMPs). Their role in renal fibrosis and renal function," Journal of Nephrology, 16: 179-185 (2003).
PCT International Search Report dated Aug. 8, 2008.
Supplemental EP Search Report dated Apr. 8, 2009.

* cited by examiner

Fig. 1

```
          10         20         30         40         50         60
MHVRSLRAAA PHSFVALWAP LFLLRSALAD FSLDNEVHSS FIHRRLRSQE RREMQREILS
          70         80         90        100        110        120
ILGLPHRPRP HLQGKHNSAP MFMLDLYNAM AVEEGGGPGG QGFSYPYKAV FSTQGPPLAS
         130        140        150        160        170        180
LQDSHFLTDA DMVMSFVNLV EHDKEFFHPR YHHREFRFDL SKIPEGEAVT AAEFRIYKDY
         190        200        210        220        230        240
IRERFDNETF RISVYQVLQE HLGRESDLFL LDSRTLWASE EGWLVFDITA TSNHWVVNPR
         250        260        270        280        290        300
HNLGLQLSVE TLDGQSINPK LAGLIGRHGP QNKQPFMVAF FKATEVHFRS IRSTGSKQRS
         310        320        330        340        350        360
QNRSKTPKNQ EALRMANVAE NSSSDQRQAC KKHELYVSFR DLGWQDWIIA PEGYAAYYCE
         370        380        390        400        410        420
GECAFPLNSY MNATNHAIVQ TLVHFINPET VPKPCCAPTQ LNAISVLYFD DSSNVILKKY
         430
RNMVVRACGC H
```

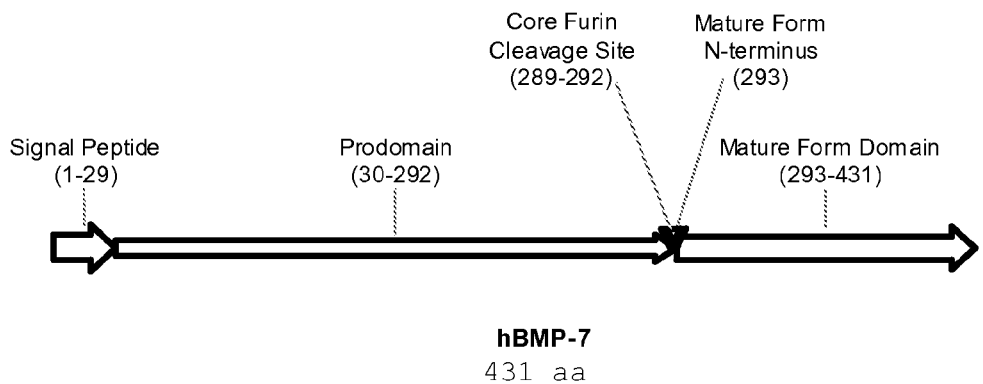

hBMP-7
431 aa

US 7,659,250 B2

BMP-7 VARIANT COMPOSITIONS, METHODS AND USES

CROSS-REFERENCE TO RELATED APPLICATION

This application is a continuation-in-part of International Application Number PCT/US2006/048730, with international filing date of 20 Dec. 2006, which claims priority to U.S. Provisional Application No. 60/752,969, filed 22 Dec. 2005. The instant application also claims priority to U.S. Provisional Application No. 60/820,538, filed 27 Jul. 2006. The entire content of each of the aforementioned applications is incorporated herein by reference in their entirety.

FIELD OF THE INVENTION

The present invention relates to human Bone Morphogenic Protein 7 (hBMP-7) variant peptide chains, nucleic acid chains encoding these peptide chains, and methods of making and using the foregoing.

BACKGROUND OF THE INVENTION

Human Bone Morphogenic Protein 7 (hBMP-7) is a member of the TGF-β superfamily of proteins and has recognized therapeutic potential as both a modulator of bone structure and renal function (Klahr, J. Nephrol. 16:179-185 (2003)). For example, active hBMP-7 could be used as a protein therapeutic in indications such as myelofibrosis, idiopathic pulmonary fibrosis, renal osteodystrophy, renal fibrosis, diabetic nephropathy, chronic obstructive pulmonary disorder (COPD), and osteoarthritis.

hBMP-7 is transcribed as mRNA containing a 1293 base pair open reading frame (the corresponding cDNA is shown at SEQ ID NO: 1) which is translated as a precursor protein of 431 amino acid residues (FIG. 1; SEQ ID NO: 2) that is proteolytically processed. The hBMP-7 precursor protein contains a signal peptide spanning residues 1 to 29 of SEQ ID NO: 2, a prodomain spanning residues 30-292 of SEQ ID NO: 2, and a mature form domain spanning residues 293-431 of SEQ ID NO: 2 (FIG. 1).

Proteolytic processing of the hBMP-7 precursor protein is believed to occur in several steps. First, the signal peptide directs hBMP-7 to the endoplasmic reticulum of the cell where folding occurs and hBMP-7 forms a homodimeric protein complex. Next, the hBMP-7 prodomain is removed by proteolytic processing to produce a covalently linked homodimer consisting of two antiparallel hBMP-7 mature domain peptide chains. This final homodimeric protein complex is the biologically active form and secreted by cells.

Secreted hBMP-7 interacts with surface receptors on other cells and soluble antagonists, such as ActRII, BMPR1a, and Noggin to mediate its biological effects and activity. Structural information concerning these interactions can be derived from a number of different BMP-7 crystal structures (Greenwald et al., Mol. Cell. 11:605-017 (2003); Griffith et al., PNAS. 93:878-883 (1996); Keller et al., Nat. Struct. Mol. Biol. 5:481-488 (2004); Groppe et al., Nature. 420(6916): 636-642 (2002).

Although hBMP-7 (formerly known as osteogenic protein 1 (OP-1) by Ozkaynak et al. (EMBO J. 9(7), 2085-2093 (1990)) has been known at least since 1990, to date several unresolved problems have prevented its development as a therapeutic protein. First, recombinant expression of hBMP-7 in mammalian cells is extremely low relative to other proteins of similar size. This is incompatible with the large-scale commercial production and purification needed for therapeutic use of hBMP-7. Second, proteolytic processing of the mature domain of hBMP-7 can occur at any of four different sites in that domain. This results in a number of different mature forms of hBMP-7 being produced during the recombinant expression of this protein. This high degree of heterogeneity in the expressed protein is highly undesirable in a protein therapeutic. Third, the mature form of hBMP-7 has poor solubility at pH values near 7.0; thus, acidic pH values are required to maintain hBMP-7 solubility. However, acidic pH values are incompatible with most common delivery methods, such as intravenous injection, used to administer protein therapeutics to patients. Lastly, the prodomain of hBMP-7 associates non-covalently with the mature domain of hBMP-7. Thus, purifying the prodomain away from the mature domain of hBMP-7 is relatively difficult and is incompatible with large-scale commercial production and purification.

Thus, a need exists for hBMP-7 variant peptide chains with improved properties that are suitable for use as therapeutic proteins and are compatible with large-scale commercial production and purification.

BRIEF DESCRIPTION OF THE DRAWINGS

FIG. 1 shows the wild-type hBMP-7 precursor amino acid sequence and hBMP-7 amino acid sequence feature map. Underlined bold text denotes the amino terminus of mature hBMP-7.

SUMMARY OF THE INVENTION

Figure 2:
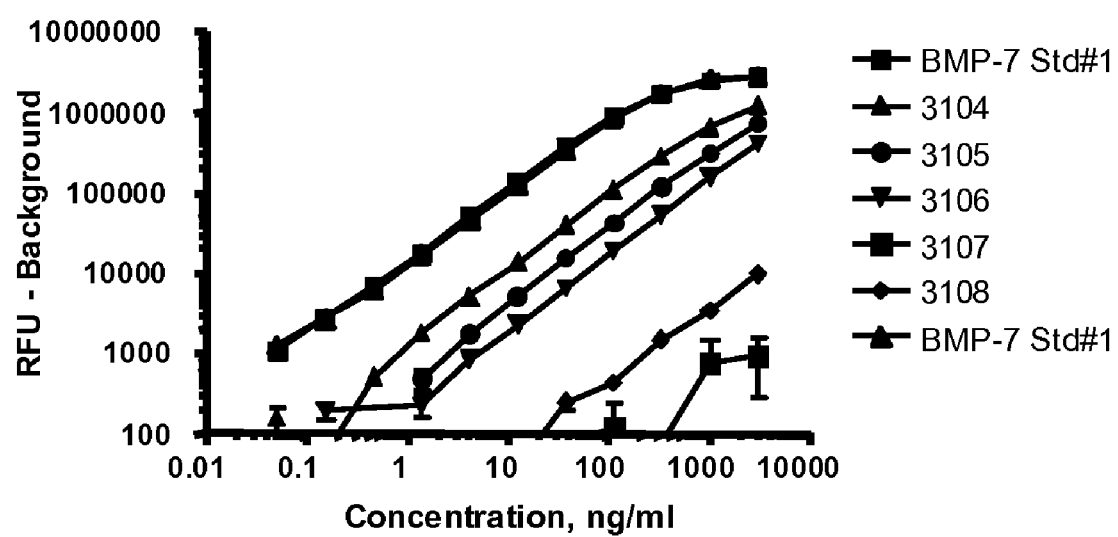
FIG. 2 shows expression of hBMP-7 variants encoded by p3104, p3105, p3106, p3107, and p3108 as assayed by sandwich-type ELISA.

One aspect of the invention is an isolated peptide chain comprising the amino acid sequence shown in SEQ ID NO: 4.

Another aspect of the invention is an isolated peptide chain comprising the amino acid sequence shown in SEQ ID NO: 6.

Another aspect of the invention is an isolated peptide chain comprising the amino acid sequence shown in SEQ ID NO: 8.

Another aspect of the invention is an isolated peptide chain comprising the amino acid sequence shown in SEQ ID NO: 10.

Another aspect of the invention is an isolated peptide chain comprising the amino acid sequence shown in SEQ ID NO: 12.

Another aspect of the invention is an isolated peptide chain comprising the amino acid sequence shown in SEQ ID NO: 14.

Another aspect of the invention is an isolated peptide chain comprising the amino acid sequence shown in SEQ ID NO: 16.

Another aspect of the invention is an isolated peptide chain comprising the amino acid sequence shown in SEQ ID NO: 18.

Another aspect of the invention is an isolated peptide chain comprising the amino acid sequence shown in SEQ ID NO: 20.

Another aspect of the invention is an isolated peptide chain comprising the amino acid sequence shown in SEQ ID NO: 22.

Another aspect of the invention is an isolated peptide chain comprising the amino acid sequence shown in SEQ ID NO: 24.

Another aspect of the invention is an isolated peptide chain comprising the amino acid sequence shown in SEQ ID NO: 26.

Another aspect of the invention is an isolated peptide chain comprising the amino acid sequence shown in SEQ ID NO: 28.

Another aspect of the invention is an isolated peptide chain comprising the amino acid sequence shown in SEQ ID NO: 30.

Another aspect of the invention is an isolated peptide chain comprising the amino acid sequence shown in SEQ ID NO: 32.

Another aspect of the invention is an isolated peptide chain comprising the amino acid sequence shown in SEQ ID NO: 34.

Another aspect of the invention is an isolated peptide chain comprising the amino acid sequence shown in SEQ ID NO: 36.

Another aspect of the invention is an isolated peptide chain comprising the amino acid sequence shown in SEQ ID NO: 38.

Another aspect of the invention is an isolated peptide chain comprising the amino acid sequence shown in SEQ ID NO: 40.

Another aspect of the invention is an isolated peptide chain comprising the amino acid sequence shown in SEQ ID NO: 42.

Another aspect of the invention is an isolated peptide chain comprising the amino acid sequence shown in SEQ ID NO: 44.

Another aspect of the invention is an isolated peptide chain comprising the amino acid sequence shown in SEQ ID NO: 46.

Another aspect of the invention is an isolated peptide chain comprising the amino acid sequence shown in SEQ ID NO: 48.

Another aspect of the invention is an isolated nucleic acid comprising the nucleic acid sequence shown in SEQ ID NO: 3.

Another aspect of the invention is an isolated nucleic acid comprising the nucleic acid sequence shown in SEQ ID NO: 5.

Another aspect of the invention is an isolated nucleic acid comprising the nucleic acid sequence shown in SEQ ID NO: 7.

Another aspect of the invention is an isolated nucleic acid comprising the nucleic acid sequence shown in SEQ ID NO: 9.

Another aspect of the invention is an isolated nucleic acid comprising the nucleic acid sequence shown in SEQ ID NO: 11.

Another aspect of the invention is an isolated nucleic acid comprising the nucleic acid sequence shown in SEQ ID NO: 13.

Another aspect of the invention is an isolated nucleic acid comprising the nucleic acid sequence shown in SEQ ID NO: 15.

Another aspect of the invention is an isolated nucleic acid comprising the nucleic acid sequence shown in SEQ ID NO: 17.

Another aspect of the invention is an isolated nucleic acid comprising the nucleic acid sequence shown in SEQ ID NO: 19.

Another aspect of the invention is an isolated nucleic acid comprising the nucleic acid sequence shown in SEQ ID NO: 21.

Another aspect of the invention is an isolated nucleic acid comprising the nucleic acid sequence shown in SEQ ID NO: 23.

Another aspect of the invention is an isolated nucleic acid comprising the nucleic acid sequence shown in SEQ ID NO: 25.

Another aspect of the invention is an isolated nucleic acid comprising the nucleic acid sequence shown in SEQ ID NO: 27.

Another aspect of the invention is an isolated nucleic acid comprising the nucleic acid sequence shown in SEQ ID NO: 29.

Another aspect of the invention is an isolated nucleic acid comprising the nucleic acid sequence shown in SEQ ID NO: 31.

Another aspect of the invention is an isolated nucleic acid comprising the nucleic acid sequence shown in SEQ ID NO: 33.

Another aspect of the invention is an isolated nucleic acid comprising the nucleic acid sequence shown in SEQ ID NO: 35.

Another aspect of the invention is an isolated nucleic acid comprising the nucleic acid sequence shown in SEQ ID NO: 37.

Another aspect of the invention is an isolated nucleic acid comprising the nucleic acid sequence shown in SEQ ID NO: 39.

Another aspect of the invention is an isolated nucleic acid comprising the nucleic acid sequence shown in SEQ ID NO: 41.

Another aspect of the invention is an isolated nucleic acid comprising the nucleic acid sequence shown in SEQ ID NO: 43.

Another aspect of the invention is an isolated nucleic acid comprising the nucleic acid sequence shown in SEQ ID NO: 45.

Another aspect of the invention is an isolated nucleic acid comprising the nucleic acid sequence shown in SEQ ID NO: 47.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a cell" is a reference to one or more cells and includes equivalents thereof known to those skilled in the art.

Unless defined otherwise, all technical and scientific terms used herein have the same meaning as commonly understood by one of ordinary skill in the art to which this invention belongs. Although any compositions and methods similar or equivalent to those described herein can be used in the practice or testing of the invention, exemplary compositions and methods are described herein.

The term "peptide chain" means a molecule comprising at least two amino acid residues linked by a peptide bond to form a chain. Large peptide chains of more than 50 amino acids may be referred to as "polypeptides" or "proteins." Small peptide chains of less than 50 amino acids may be referred to as "peptides."

The term "nucleic acid" means a molecule comprising at least two nucleic acid residues linked to form a chain. Such nucleic acid residues may be those found in DNA or RNA. Small nucleic acids of less than 50 residues may be referred to as "oligonucleotides."

The term "hBMP-7 responsive condition" means a pathological condition that is responsive to a biological activity of a hBMP-7 peptide chain or a hBMP-7 variant peptide chain. Such peptide chains may comprise a fragment of SEQ ID NO: 2 or a peptide chain of the invention. Examples of hBMP-7 activity responsive pathological conditions include, for example, myelofibrosis, idiopathic pulmonary fibrosis, renal osteodystrophy, diabetic nephropathy, chronic obstructive pulmonary disorder (COPD), and osteoarthritis. Biological activities resulting from hBMP-7 peptide chain or a hBMP-7 variant peptide chain include, for example, induction of bone formation, increased alkaline phosphatase activity, increased hyaluronan synthase 2 mRNA levels, increased type I collagen mRNA levels, increased osteocalcin synthesis, and inhibition of TGF-β induced cell proliferation. Those skilled in the art will recognize many other such biological activities and pathological conditions.

The invention provides isolated peptide chain hBMP-7 variant compositions, nucleic acids encoding these compositions, and related methods. The compositions and methods of the invention will be useful in controlling cell proliferation and in the treatment of hBMP-7 responsive conditions such as myelofibrosis, idiopathic pulmonary fibrosis, renal osteodystrophy, diabetic nephropathy, chronic obstructive pulmonary disorder (COPD), and osteoarthritis.

All peptide chains and nucleic acids of the invention were derived by mutagenesis using standard in vitro or in vivo methods, or combinations of such methods, from the cDNA (SEQ ID NO: 1) encoding the wild-type hBMP-7 precursor peptide chain of SEQ ID NO: 2. All mutated positions in the hBMP-7 variant peptide chains of the invention are described herein by referencing the position of the amino acid residue that has been changed in the wild-type hBMP-7 precursor peptide chain of SEQ ID NO: 2. Conventional one and three-letter amino acid codes are used herein as follows:

| Amino acid | Three-letter code | One-letter code |
| --- | --- | --- |
| Alanine | ala | A |
| Arginine | arg | R |
| Asparagine | asn | N |
| Aspartate | asp | D |
| Cysteine | cys | C |
| Glutamate | glu | E |
| Glutamine | gln | Q |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |

-continued

| Amino acid | Three-letter code | One-letter code |
| --- | --- | --- |
| Tyrosine | tyr | Y |
| Valine | val | V |

Single letter amino acid abbreviations are used to describe the nature of the change. For example, R299S denotes that the R (arginine) amino acid at position 299 of SEQ ID NO: 2 has been changed to an S (serine) amino acid and ΔS293-R299 indicates that the amino acid sequence starting at S amino acid at position 293 of SEQ ID NO: 2 and ending at the R at position 299 of SEQ ID NO: 2 has been deleted.

Wild-type hBMP-7 (SEQ ID NO: 2) has several important properties and features which may be modified by mutation. First, multiple mature hBMP-7 isoforms, each with different amino termini, can be produced during proteolytic processing of the hBMP-7 precursor protein (SEQ ID NO: 2). These termini may form at S293, R299, R314, and M315 of the wild-type hBMP-7 precursor protein (SEQ ID NO: 2). The S293, R299S, R314S, ΔS293-R299, ΔS293-R314, and ΔS293-M315 mutations were each designed to prevent the formation of multiple mature hBMP-7 isoforms with different amino termini by eliminating cleavage in hBMP-7 variant peptide chains at the positions affected by each mutation. The H287R and H287T mutations flank a core furin cleavage site located in the hBMP-7 prodomain of SEQ ID NO: 2. The H287R and H287T mutations were both designed to enhance furin cleavage events that produce an amino terminus at S293 of SEQ ID NO: 2 in hBMP-7 variant peptide chains.

Second, mature hBMP-7 forms complexes with the ActRII and BMPPR1a receptor proteins. The L407K, F409K, L417R, L382K, L382N, V383K, I386R, and I386N mutations were designed to decrease the surface hydrophobicity of hBMP-7 variant peptide chains while at the same time minimizing any disruption to hBMP-7 variant:ActRII or hBMP-7 variant:BMPPR1a peptide chain complex formation. Such decreased surface hydrophobicity in hBMP-7 variant peptide chains is designed to reduce the formation of aggregates by variants containing these mutations while still permitting hBMP-7 mediated signaling through the ActRII and BMPPR1a receptor proteins.

Third, mature hBMP-7 can be bound by the soluble antagonist protein Noggin. The W347D mutation was designed to decrease hBMP-7 variant peptide chain binding to Noggin to enhance hBMP-7 mediated signaling and biological activity.

Additionally, mutations at R421, N422, and R426 of hBMP-7 may increase expression of the resulting hBMP-7 variant peptide chain. Without wishing to be limited by any theory, it is believed that mutations such as R421E, N422D, and R426E improve hBMP-7 variant peptide chain expression by increasing the solubility of the expressed peptide chain.

Further, the pharmacological properties of hBMP-7 variant peptide chains, such as in vivo half-life, may be improved by pegylation. The S293C mutation is designed to create an amino terminal C residue in the mature form of the hBMP-7 variant peptide chains containing this mutation. This amino terminal C residue can then be post-translationally modified by the covalent attachment of polyethylene glycol by techniques known to those skilled in the art.

Last, deletion and domain replacement mutants derived from the wild-type hBMP-7 precursor peptide chain of SEQ ID NO: 2 can be designed to improve hBMP-7 variant peptide chain expression. One such hBMP-7 variant peptide chain mutant comprises the hBMP-7 signal peptide and prodomain alone, but lacks the hBMP-7 mature form domain which has been deleted. Another such mutant comprises the human growth hormone signal peptide (residues M1 to A26 of SEQ ID NO: 38) which replaces the native hBMP-7 secretory signal peptide, lacks the hBMP-7 prodomain which has been deleted, and contains the R299S and R314S mutations in the hBMP-7 mature form domain. Another mutant comprises the human BMP-2 (hBMP-2) secretory signal peptide instead of the native hBMP-7 secretory signal peptide, the hBMP-2 prodomain instead of the native hBMP-7 prodomain, and the R299S and R314S mutations in the hBMP-7 mature form domain. Another mutant comprises the hBMP-2 secretory signal peptide instead of the native hBMP-7 secretory signal peptide, hBMP-2 prodomain instead of the native hBMP-7 prodomain, and the R299S, R314S, R421E, N422D, and R426E mutations in the hBMP-7 mature form domain. These hBMP-7 variant peptide chain mutants were designed, in part, to facilitate improved secretion, proteolytic processing and expression of hBMP-7.

Each individual mutation described herein, such as point mutations, deletions, or domain replacements can be used alone or in combination to produce the peptide chains of the invention. The mutations described here may also be combined to generate additional variant BMP-7 peptide chains having modified properties corresponding, in part, to the various individual mutations described herein. Nucleic acids encoding such additional variant peptide chains may be generated using standard in vitro or in vivo methods, or combinations of such methods, well known in the art. The peptide chains of the invention may also be post-translationally modified by the addition of one or more covalent modifications such as, for example, the addition of polyethylene glycol to the amino terminus or other portions of the peptide chains of the invention. Lastly, the signal peptide and prodomain sequences of the variant peptides of the invention may be replaced with functionally equivalent amino acid sequences. Functional equivalents of the point mutations described here may be generated by replacing the amino acid residue at the site of a particular point mutation with a different amino acid residue. Such additional variants and the nucleic acids encoding them are also within the scope of the invention. Similarly, variant peptide chains comprising mutated mature domain peptide chains alone and the nucleic acids encoding them are also within the scope of the invention.

One aspect of the invention is an isolated peptide chain comprising the amino acid sequence shown in SEQ ID NO: 4. The peptide chain of SEQ ID NO: 4 was derived from the wild-type hBMP-7 precursor peptide chain of SEQ ID NO: 2 and contains the R299S the R314S mutations.

Another aspect of the invention is an isolated peptide chain comprising the amino acid sequence shown in SEQ ID NO: 6. The peptide chain of SEQ ID NO: 6 was derived from the wild-type hBMP-7 precursor peptide chain of SEQ ID NO: 2 and contains the ΔS293-R299, and R314S mutations.

Another aspect of the invention is an isolated peptide chain comprising the amino acid sequence shown in SEQ ID NO: 8. The peptide chain of SEQ ID NO: 8 was derived from the wild-type hBMP-7 precursor peptide chain of SEQ ID NO: 2 and contains the ΔS293-M314 mutation.

Another aspect of the invention is an isolated peptide chain comprising the amino acid sequence shown in SEQ ID NO: 10. The peptide chain of SEQ ID NO: 10 was derived from the wild-type hBMP-7 precursor peptide chain of SEQ ID NO: 2 and contains the ΔS293-M315 mutation.

Another aspect of the invention is an isolated peptide chain comprising the amino acid sequence shown in SEQ ID NO: 12. The peptide chain of SEQ ID NO: 12 was derived from the wild-type hBMP-7 precursor peptide chain of SEQ ID NO: 2 and contains the R299S, R314S, and L407K mutations.

Another aspect of the invention is an isolated peptide chain comprising the amino acid sequence shown in SEQ ID NO: 14. The peptide chain of SEQ ID NO: 14 was derived from the wild-type hBMP-7 precursor peptide chain of SEQ ID NO: 2 and contains the R299S, R314S, and F409K mutations.

Another aspect of the invention is an isolated peptide chain comprising the amino acid sequence shown in SEQ ID NO: 16. The peptide chain of SEQ ID NO: 16 was derived from the wild-type hBMP-7 precursor peptide chain of SEQ ID NO: 2 and contains the R299S, R314S, and L417R mutations.

Another aspect of the invention is an isolated peptide chain comprising the amino acid sequence shown in SEQ ID NO: 18. The peptide chain of SEQ ID NO: 18 was derived from the wild-type hBMP-7 precursor peptide chain of SEQ ID NO: 2 and contains the R299S, R314S, and L382K mutations.

Another aspect of the invention is an isolated peptide chain comprising the amino acid sequence shown in SEQ ID NO: 20. The peptide chain of SEQ ID NO: 20 was derived from the wild-type hBMP-7 precursor peptide chain of SEQ ID NO: 2 and contains the R299S, R314S, and L382N mutations.

Another aspect of the invention is an isolated peptide chain comprising the amino acid sequence shown in SEQ ID NO: 22. The peptide chain of SEQ ID NO: 22 was derived from the wild-type hBMP-7 precursor peptide chain of SEQ ID NO: 2 and contains the R299S, R314S, and V383K mutations.

Another aspect of the invention is an isolated peptide chain comprising the amino acid sequence shown in SEQ ID NO: 24. The peptide chain of SEQ ID NO: 24 was derived from the wild-type hBMP-7 precursor peptide chain of SEQ ID NO: 2 and contains the R299S, R314S, and I386R mutations.

Another aspect of the invention is an isolated peptide chain comprising the amino acid sequence shown in SEQ ID NO: 26. The peptide chain of SEQ ID NO: 26 was derived from the wild-type hBMP-7 precursor peptide chain of SEQ ID NO: 2 and contains the R299S, R314S, and I386N mutations.

Another aspect of the invention is an isolated peptide chain comprising the amino acid sequence shown in SEQ ID NO: 28. The peptide chain of SEQ ID NO: 28 was derived from the wild-type hBMP-7 precursor peptide chain of SEQ ID NO: 2 and contains the R299S, R314S, V383K, L407K, and F409K mutations.

Another aspect of the invention is an isolated peptide chain comprising the amino acid sequence shown in SEQ ID NO: 30. The peptide chain of SEQ ID NO: 30 was derived from the wild-type hBMP-7 precursor peptide chain of SEQ ID NO: 2 and contains the R299S, R314S, and W347D mutations.

Another aspect of the invention is an isolated peptide chain comprising the amino acid sequence shown in SEQ ID NO: 32. The peptide chain of SEQ ID NO: 32 was derived from the wild-type hBMP-7 precursor peptide chain of SEQ ID NO: 2 and contains the R299S, R314S, R421E, N422D and R426E mutations.

Another aspect of the invention is an isolated peptide chain comprising the amino acid sequence shown in SEQ ID NO: 34. The peptide chain of SEQ ID NO: 34 was derived from the wild-type hBMP-7 precursor peptide chain of SEQ ID NO: 2 and contains the S293C, R299S, and R314S mutations.

In one embodiment the invention provides an isolated peptide chain comprising the amino acid sequence shown in SEQ ID NO: 34 further comprising at least one polyethylene glycol molecule. Such a polyethylene glycol residue may be covalently linked to C293 of SEQ ID NO: 34 for example.

C293 is expected to be the amino terminal residue in the mature form of SEQ ID NO: 34 resulting from proteolytic processing.

Another aspect of the invention is an isolated peptide chain comprising the amino acid sequence shown in SEQ ID NO: 36. The peptide chain of SEQ ID NO: 36 was derived from the wild-type hBMP-7 precursor peptide chain of SEQ ID NO: 2. The peptide chain of SEQ ID NO: 36 comprises the hBMP-7 signal peptide (residues M1 to A29 of SEQ ID NO: 2) and prodomain alone (residues D30 to R292 of SEQ ID NO: 20); the hBMP-7 mature form domain (residues S293 to H431 of SEQ ID NO: 2) has been deleted.

Another aspect of the invention is an isolated peptide chain comprising the amino acid sequence shown in SEQ ID NO: 38. The peptide chain of SEQ ID NO: 38 was derived, in part, from the wild-type hBMP-7 precursor peptide chain of SEQ ID NO: 2. The peptide chain of SEQ ID NO: 38 comprises a human growth hormone signal peptide (residues M1 to A26 of SEQ ID NO: 38), lacks the hBMP-7 prodomain, and contains the R299S and R314S mutations in the hBMP-7 mature form domain.

Another aspect of the invention is an isolated peptide chain comprising the amino acid sequence shown in SEQ ID NO: 40. The peptide chain of SEQ ID NO: 40 was derived, in part, from the wild-type hBMP-7 precursor peptide chain of SEQ ID NO: 2. The peptide chain of SEQ ID NO: 40 comprises the hBMP-2 secretory signal peptide instead of the native hBMP-7 secretory signal peptide, hBMP-2 prodomain instead of the native hBMP-7 prodomain, and the R299S and R314S mutations in the hBMP-7 mature form domain.

Another aspect of the invention is an isolated peptide chain comprising the amino acid sequence shown in SEQ ID NO: 42. The peptide chain of SEQ ID NO: 42 was derived from the wild-type hBMP-7 precursor peptide chain of SEQ ID NO: 2. The peptide chain of SEQ ID NO: 42 contains the H287R, R299S, R314S, R421E, N422D, and R426E mutations.

Another aspect of the invention is an isolated peptide chain comprising the amino acid sequence shown in SEQ ID NO: 44. The peptide chain of SEQ ID NO: 44 was derived, in part, from the wild-type hBMP-7 precursor peptide chain of SEQ ID NO: 2. The peptide chain of SEQ ID NO: 44 comprises the hBMP-2 secretory signal peptide instead of the native hBMP-7 secretory signal peptide, hBMP-2 prodomain instead of the native hBMP-7 prodomain, and the R299S, R314S, R421E, N422D, and R426E mutations in the hBMP-7 mature form domain.

Another aspect of the invention is an isolated peptide chain comprising the amino acid sequence shown in SEQ ID NO: 46. The peptide chain of SEQ ID NO: 46 was derived from the wild-type hBMP-7 precursor peptide chain of SEQ ID NO: 2. The peptide chain of SEQ ID NO: 46 contains the H287T, R299S, and R314S mutations.

Another aspect of the invention is an isolated peptide chain comprising the amino acid sequence shown in SEQ ID NO: 48. The peptide chain of SEQ ID NO: 48 was derived from the wild-type hBMP-7 precursor peptide chain of SEQ ID NO: 2. The peptide chain of SEQ ID NO: 48 contains the H287R, R299S, and R314S mutations.

One embodiment of the invention is an isolated nucleic acid comprising a nucleic acid sequence encoding a peptide chain of the invention. Such nucleic acids may be generated using standard in vitro or in vivo methods, or combinations of such methods, well known in the art. Such nucleic acids may comprise alternative codons encoding the amino acids of the peptide chains of the invention or organism optimized codons encoding the amino acids of the peptide chains of the invention.

Another aspect of the invention is an isolated nucleic acid comprising the nucleic acid sequence shown in SEQ ID NO: 3.

Another aspect of the invention is an isolated nucleic acid comprising the nucleic acid sequence shown in SEQ ID NO: 5.

Another aspect of the invention is an isolated nucleic acid comprising the nucleic acid sequence shown in SEQ ID NO: 7.

Another aspect of the invention is an isolated nucleic acid comprising the nucleic acid sequence shown in SEQ ID NO: 9.

Another aspect of the invention is an isolated nucleic acid comprising the nucleic acid sequence shown in SEQ ID NO: 11.

Another aspect of the invention is an isolated nucleic acid comprising the nucleic acid sequence shown in SEQ ID NO: 13.

Another aspect of the invention is an isolated nucleic acid comprising the nucleic acid sequence shown in SEQ ID NO: 15.

Another aspect of the invention is an isolated nucleic acid comprising the nucleic acid sequence shown in SEQ ID NO: 17.

Another aspect of the invention is an isolated nucleic acid comprising the nucleic acid sequence shown in SEQ ID NO: 19.

Another aspect of the invention is an isolated nucleic acid comprising the nucleic acid sequence shown in SEQ ID NO: 21.

Another aspect of the invention is an isolated nucleic acid comprising the nucleic acid sequence shown in SEQ ID NO: 23.

Another aspect of the invention is an isolated nucleic acid comprising the nucleic acid sequence shown in SEQ ID NO: 25.

Another aspect of the invention is an isolated nucleic acid comprising the nucleic acid sequence shown in SEQ ID NO: 27.

Another aspect of the invention is an isolated nucleic acid comprising the nucleic acid sequence shown in SEQ ID NO: 29.

Another aspect of the invention is an isolated nucleic acid comprising the nucleic acid sequence shown in SEQ ID NO: 31.

Another aspect of the invention is an isolated nucleic acid comprising the nucleic acid sequence shown in SEQ ID NO: 33.

Another aspect of the invention is an isolated nucleic acid comprising the nucleic acid sequence shown in SEQ ID NO: 35.

Another aspect of the invention is an isolated nucleic acid comprising the nucleic acid sequence shown in SEQ ID NO: 37.

Another aspect of the invention is an isolated nucleic acid comprising the nucleic acid sequence shown in SEQ ID NO: 39.

Another aspect of the invention is an isolated nucleic acid comprising the nucleic acid sequence shown in SEQ ID NO: 41.

Another aspect of the invention is an isolated nucleic acid comprising the nucleic acid sequence shown in SEQ ID NO: 43.

Another aspect of the invention is an isolated nucleic acid comprising the nucleic acid sequence shown in SEQ ID NO: 45.

Another aspect of the invention is an isolated nucleic acid comprising the nucleic acid sequence shown in SEQ ID NO: 47.

Another embodiment of the invention is a method of inhibiting TGF-β induced cell proliferation comprising providing a peptide chain of the invention to a cell. The peptide chains of the invention may be provided to cells that are, for example, eukaryotic cells. The peptide chains of the invention can be administered by any technique that provides such molecules to a cell. A peptide chain can be provided to a cell in vitro by, for example, supplementing the culture medium with the peptide chain or a nucleic acid chain encoding the peptide chain. Peptide chains may also be provided to a cell by transfecting a nucleic acid chain encoding the peptide chain into the cell. A peptide chain may be provided to a cell in vivo by, for example, intravenous injection of the peptide chain or a nucleic acid encoding the peptide chain into an animal or tissue. Those skilled in the art will recognize other means for administering the peptide chains of the invention to a cell in vitro or in vivo. Such means also include those modes for delivery of an agent to a host that are discussed below.

Another embodiment of the invention is a vector comprising at least one nucleic acid of the invention. Such vectors permit a nucleic acid of the invention to be introduced into a cell, animal or other nucleic acid replication system and expression systems, such as an in vitro transcription and translation system. For example a vector of the invention may comprise portions of a transposon, plasmid, virus, or chromosome that, alone or when combined, permit a nucleic acid of the invention to be introduced into a cell or other system. A wide variety of such vectors are well known to those skilled in the art.

Another embodiment of the invention is a host cell comprising a vector of the invention. Such host cells may be eukaryotic cells, bacterial cells, plant cells or archeal cells. Exemplary eukaryotic cells may be of mammalian, insect, avian or other animal origins. An exemplary mammalian eukaryotic cell line is the HEK-293 (American Type Culture Collection, Manassas, Va.; ATCC® Number: CRL-1573™) cell line. Other useful cell lines include those derived from Chinese Hamster Ovary (CHO) cells such as CHO-K1 (ATCC® Number: CRL-61™) and rat osteosarcoma (ROS) cells such as ROS 27/2.8 cells. Mammalian eukaryotic cells also include immortalized cell lines such as hybridomas or myeloma cell lines such as SP2/0 (ATCC® Number: CRL-1581™), NS0 (European Collection of Cell Cultures (ECACC), Salisbury, Wiltshire, UK, ECACC No. 85110503), FO (ATCC® Number: CRL-1646™) and Ag653 (ATCC® Number: CRL-1580™) murine cell lines. An exemplary human myeloma cell line is U266 (ATCC® Number: CRL-TIB-196™).

Another embodiment of the invention is a method of making a peptide chain comprising culturing a host cell of the invention and recovering the peptide chain produced by the host cell. Standard cell culture and enzymology methods well known in the art may be used to culture a host cell of the invention and to recover peptide chains produced by such host cells.

Another embodiment of the invention is a method of making a peptide chain comprising expressing an isolated peptide chain comprising the amino acid sequence shown in SEQ ID NO: 4, SEQ ID NO: 6, SEQ ID NO: 8, or SEQ ID NO: 42 in an expression system and recovering a peptide chain wherein the peptide chain is capable of either increasing alkaline phosphatase activity in ROS 17/2.8 cells relative to negative control ROS 17/2.8 cells that did not receive the peptide chain or increasing the number of viable VEPT cells relative to negative control VEPT cells that did not receive the peptide chain. Expression systems useful in the method of the invention may be, for example, an in vitro coupled transcription and translation system, or a cell or other expression system, such as an animal or plant.

hBMP-7 mature form activity can be detected by assaying for increased alkaline phosphatase activity in rat osteosarcoma 17/2.8 (ROS 17/2.8) cells treated with the mature form of hBMP-7 relative to untreated control ROS 17/2.8 cells. A peptide chain capable of increasing alkaline phosphatase activity in ROS 17/2.8 cells has hBMP-7 activity. Alkaline phosphatase based hBMP-7 assays using ROS 17/2.8 cells can be performed using standard cell culture and enzymology methods well known in the art such as, for example, those described by Maliakal et al., Growth Factors. 112(3):227-234 (1994).

hBMP-7 mature form activity can also be detected by assaying for increased numbers of viable VEPT cells after treatment with the mature form of hBMP-7 relative to untreated negative control VEPT cells. A peptide chain capable of increasing the numbers of viable VEPT cells in a population has hBMP-7 activity. Cell viability based hBMP-7 assays using ROS 17/2.8 cells can be performed using standard cell culture and enzymology methods well known in the art. Those skilled in the art will also recognize that such assays for hBMP-7 activity may also be used to confirm the biological activity and effect of the compositions and methods of the invention.

Those skilled in the art will also recognize that the assays for hBMP-7 activity described above may also be used to confirm the biological activity and effect of the compositions and methods of the invention.

Another embodiment of the invention is a method of treatment comprising the steps of identifying an animal with an hBMP-7 responsive condition; and administering the peptide chain of the invention to the animal in an amount sufficient to attenuate the pathological condition. Examples of hBMP-7 activity responsive pathological conditions include, for example, myelofibrosis, idiopathic pulmonary fibrosis, renal osteodystrophy, diabetic nephropathy, chronic obstructive pulmonary disorder (COPD), and osteoarthritis.

The methods of treatment of the invention may be used to treat an animal patient belonging to any classification. Examples of such animals include mammals such as humans, rodents, dogs, cats and farm animals and other animal classes such as birds, reptiles and fish.

The mode of administration for therapeutic use of the peptide chains of the invention may be any suitable route that delivers the peptide chain to the host. The peptide chains and nucleic acid chains of the invention are particularly useful for parenteral administration, i.e., subcutaneously, intramuscularly, intradermally, intravenously or intranasally.

Peptide chains and nucleic acids of the invention may be prepared as pharmaceutical compositions containing an effective amount of the peptide chain or nucleic acid as an active ingredient in a pharmaceutically acceptable carrier. An aqueous suspension or solution containing the peptide chain or nucleic acid, preferably buffered at physiological pH, in a form ready for injection is preferred. The compositions for parenteral administration will commonly comprise a solution of the antagonist of the invention or a cocktail thereof dissolved in an pharmaceutically acceptable carrier, preferably an aqueous carrier. A variety of aqueous carriers may be employed, e.g., 0.4% saline, 0.3% glycine and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions such as pH adjusting and buffering agents, etc. The concentration of the peptide chains or nucleic acid chains of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition for intramuscular injection could be prepared to contain 1 mL sterile buffered water, and between about 1 ng to about 100 mg, e.g. about 50 ng to about 30 mg or more preferably, about 5 mg to about 25 mg, of a peptide chain or nucleic acid of the invention. Similarly, a pharmaceutical composition of the invention for intravenous infusion could be made up to contain about 250 ml of sterile Ringer's solution, and about 1 mg to about 30 mg and preferably 5 mg to about 25 mg of an antagonist of the invention. Actual methods for preparing parenterally administrable compositions are well known and are described in more detail in, for example, "Remington's Pharmaceutical Science", 15th ed., Mack Publishing Company, Easton, Pa.

The peptide chains and nucleic acids of the invention, when in a pharmaceutical preparation, can be present in unit dose forms. The appropriate therapeutically effective dose can be determined readily by those of skill in the art. A determined dose may, if necessary, be repeated at appropriate time intervals selected as appropriate by a physician during the treatment period.

The peptide chains or nucleic acids of the invention can be lyophilized for storage and reconstituted in a suitable carrier prior to use. This technique has been shown to be effective with conventional protein and immunoglobulin preparations and art-known lyophilization and reconstitution techniques can be employed.

The present invention will now be described with reference to the following specific, non-limiting examples.

EXAMPLE 1

Expression of hBMP-7 Variants in Mammalian HEK-293 Cells Transiently Transfected with Plasmid DNAs hBMP-7 variant proteins were recombinantly expressed in mammalian HEK-293 cells transiently transfected with plasmid DNAs encoding hexahistidine tagged forms of each variant (FIG. 2). HEK-293E cells (Invitrogen, Carlsbad, Calif.) were propagated using standard culture conditions and methods. Cells were transiently transfected with p3105, p3106, p3107 and p3108 using standard transfection methods. HEK-293E cells were also transiently transfected with p3104 as a control.

The p3104 control vector contains a cDNA (SEQ ID NO: 1) encoding the wild-type hBMP-7 precursor protein (SEQ ID NO: 2). The p3105 vector contains a cDNA (SEQ ID NO: 3) encoding the R299S/R314S hBMP-7 variant protein (SEQ ID NO: 4). The p3106 vector contains a cDNA (SEQ ID NO: 5) encoding the ΔS293-R299/R314S hBMP-7 variant protein (SEQ ID NO: 6). The p3107 vector contains a cDNA (SEQ ID NO: 7) encoding the ΔS293-R314 hBMP-7 variant protein (SEQ ID NO: 8). The p3108 vector contains a cDNA (SEQ ID NO: 9) encoding the ΔS293-M315 hBMP-7 variant protein (SEQ ID NO: 10). In each of these vectors the wild-type or variant hBMP-7 cDNA is fused in frame at its 3' end to a cDNA encoding a hexahistidine tag. Consequently, the proteins expressed by these vectors are all hexahistidine tagged at their carboxy termini.

Cell culture supernatant was collected after transfection and hexahistidine tagged proteins were purified from the supernatant using Talon™ immobilized metal affinity chromatography resin (Clontech, Inc., Mountain View, Calif.). Hexahistidine purification using Talon™ resin and preparation of supernatants was performed as directed by the manufacturer. A standard sandwich-type ELISA specific for hBMP-7 was then performed on the resulting samples (FIG. 2). This type of ELISA can be used to confirm hBMP-7 variant expression by any cell type (e.g. CHO-K1). Positive control ELISAs were also performed on purified, wild-type, hBMP-7 samples. Assay data is expressed in Relative Light Units (RLU) minus background light emission (FIG. 2; Y-axis) versus the concentration of Talon™ resin purified protein (FIG. 2; X-axis).

The ELISA data indicates that all hBMP-7 variants were expressed in mammalian HEK-293 cells from the transiently transfected vector DNAs. N-terminal sequencing analysis using standard methods demonstrated that S293 forms the amino terminus of the proteolytically processed mature form of hBMP-7 produced by in vivo expression of SEQ ID NO: 2 from p3104. Importantly, S293 was also found to form the amino terminus of the proteolytically processed form of hBMP-7 produced by in vivo expression of SEQ ID NO: 4 from p3105.

EXAMPLE 2

Expression of hBMP-7 Variants in Mammalian CHO-K1 Cells Transiently Transfected with Plasmid DNAs hBMP-7 variant proteins were recombinantly expressed in mammalian CHO-K1 cells transiently transfected with plasmid DNAs encoding each variant (FIG. 1). CHO-K1 cells (ATCC® Number: CRL-9618™) were propagated using standard culture conditions and methods. Cells were transiently transfected with p3341, p3392, p3268, or p3470 and p3199 using standard transfection methods. CHO-K1 cells were also transiently transfected with the pEMPTY negative control vector which lacked a cDNA insert encoding a hBMP-7 variant.

The p3341 positive control vector contains a cDNA (SEQ ID NO: 1) encoding the wild-type hBMP-7 precursor protein (SEQ ID NO: 2). The p3392 vector contains a cDNA (SEQ ID NO: 41) encoding an hBMP-7 variant protein (SEQ ID NO: 42) that comprises the native hBMP-7 secretory signal peptide, an hBMP-7 prodomain comprising an H287R mutation, and the R299S, R314S, R421E, N422D, and R426E mutations in the hBMP-7 mature form domain. The p3268 vector contains a cDNA (SEQ ID NO: 39) encoding an hBMP-7 variant protein (SEQ ID NO: 40) that comprises the hBMP-2 secretory signal peptide instead of the native hBMP-7 secretory signal peptide, the hBMP-2 prodomain instead of the native hBMP-7 prodomain, and the R299S and R314S mutations in the hBMP-7 mature form domain. The p3470 vector contains a cDNA (SEQ ID NO: 43) encoding an hBMP-7 variant protein (SEQ ID NO: 44) that comprises the hBMP-2 secretory signal peptide instead of the native hBMP-7 secretory signal peptide, the hBMP-2 prodomain instead of the native hBMP-7 prodomain, and the R299S, R314S, R421E, N422D and R426E mutations in the hBMP-7 mature form domain. The p3199 vector encodes, and constituatively expresses, the paired dibasic amino acid-cleaving protease enzyme (PACE) furin. Furin is the protease required for the proteolytic processing events needed to produce the mature form of hBMP-7 from hBMP-7 precursor protein. p3199 was transiently co-transfected with the vectors encoding the hBMP-7 variants encoded by p3341, p3392, p3268, or p3470 to facilitate the expression of mature, proteolytically processed hBMP-7 variant proteins.

Cell culture supernatant was collected after transfection and hBMP-7 variant proteins were purified from the supernatant using standard immunoaffinity chromatography methods. A monoclonal antibody (mAb 1B12) that specifically binds the mature form of hBMP-7 (residues 293 to 431 of SEQ ID NO: 2) was conjugated to an insoluble resin and the resulting mAb-conjugated resin was used to perform immunoaffinity chromatography using standard methods. The Sepharose 4B resin (Amersham Biosciences, Piscataway, N.J.) was activated by cyanogen bromide (CNBr) and the anti-BMP-7 mAb (1B12) was conjugated to the resin through reactive amine groups. Supernatant samples were then loaded onto chromatography columns and eluted with either a buffer at pH 2.5 containing 100 mM glycine (acid elution), or 'gentle buffer' (purchased from Pierce Biotechnology, Rockford Ill.), also referred to as "neutral elution" in one of the figures below.

Figure 3:
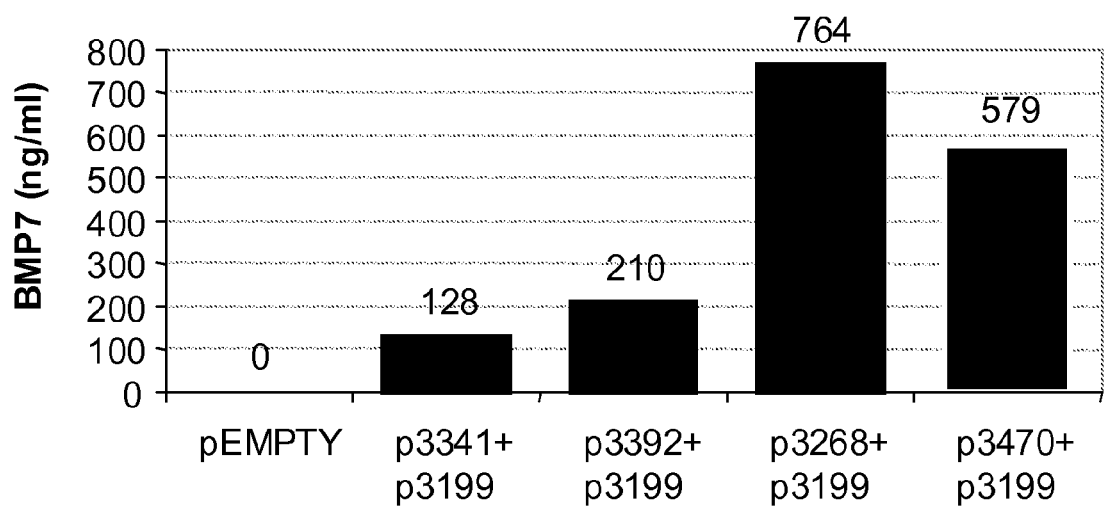
FIG. 3 shows expression of hBMP-7 variants encoded by p3341, p3392, p3268, and p3470 as assayed by sandwich-type ELISA.

A standard sandwich-type ELISA (Quantikine DBP700, R&D Systems, Minneapolis, Minn.) specific for hBMP-7 was then performed on the resulting samples (FIG. 3) according to the manufacturers instructions. Positive control ELISAs were also performed on purified wild-type hBMP-7 samples to generate a calibration curve (data not shown). Assay data is expressed in ng of BMP-7 per ml of cell culture supernatant (FIG. 3; Y-axis).

EXAMPLE 3

Expression of hBMP-7 Variant 3392 in Mammalian CHO-K1 Cells Transiently Transfected with p3392 Plasmid DNA The hBMP-7 variant peptide chain encoded by p3392 was expressed at relatively high levels (FIG. 3.) in CHO-K1 cells and was properly processed based on SDS-PAGE and Western blot analyses. The peptide chain encoded by p3392 is an hBMP-7 variant protein (SEQ ID NO: 42) that comprises the native hBMP-7 secretory signal peptide, an hBMP-7 pro-domain comprising an H287R mutation, and the R299S, R314S, R421E, N422D, and R426E mutations in the hBMP-7 mature form domain.

The hBMP-7 variant peptide (SEQ ID NO: 42) encoded by p3392 was expressed by transient transfection of CHO-K1 cells with p3392 using standard transfection and cell culture techniques. Cell culture supernatants were prepared as described in Example 2 above. The hBMP-7 variant protein expressed (SEQ ID NO: 42) by p3392 was then immunoaffinity purified by immunoaffinity chromatography as described in Example 2 above. Supernatant samples were loaded onto chromatography columns and eluted using 100 mM glycine buffer pH 2.5—acid elution, or 'gentle buffer' elution (Pierce Biotechnology, Rockford Ill.)—neutral elution. SDS-PAGE and Western blot analyses were then performed on the immunoaffinity purified hBMP-7 variant (SEQ ID NO: 42) encoded by p3392.SDS-PAGE analysis was performed using standard methods on non-reduced and reduced samples followed by Coomassie-blue staining to visual resolved protein bands. Western blot analysis was also performed using standard methods on non-reduced and reduced samples using standard methods. The hBMP-7 specific mAb described in Example 2 above was used to detect the hBMP-7 variant encoded by p3392 on the blots.

SDS-PAGE and Western blot analyses of non-reduced and reduced samples of the hBMP-7 variant encoded by p3392 revealed that this hBMP-7 variant was expressed. SDS-PAGE and Western blot analysis further indicated the presence of fully processed 15 kDa and 17 kDa mature forms the hBMP-7 variant protein (SEQ ID NO: 42) encoded by p3392 and a 48 kDa form corresponding to the unprocessed form of this hBMP-7 variant. The 15 kDa and 17 kDa forms are believed to be the product of differential post-translational modifications such as glycosylation.

Importantly, the hBMP-7 variant peptide (SEQ ID NO: 42) encoded by p3392 was expressed at relatively high levels (FIG. 3.) and was properly processed based on SDS-PAGE and Western blot analyses. This particular hBMP-7 variant protein was then selected for further bioactivity assay analyses.

EXAMPLE 4

Biological Activity of hBMP-7 Variant 3392 in an Osteosarcoma Cell Based Assay System The hBMP-7 variant protein 3392 (SEQ ID NO: 42) is biologically active when recombinantly expressed in CHO-K1 cells (FIG. 4) and assayed in an osteosarcoma cell based assay system. This variant protein also has biological activity comparable to that of wild-type hBMP-7 provided at an identical concentration (FIG. 4).

hBMP-7 mature form biological activity was assayed using a rat osteosarcoma 17/2.8 cell alkaline phosphatase induction assay. Biologically active hBMP-7 induces alkaline phosphatase expression by ROS 17/2.8 cells. ROS 17/2.8 cells are capable of causing bone formation by osteogenesis and increased alkaline phosphatase activity is a hallmark of the induction of osteogenesis.

ROS 17/2.8 cells were seeded at a density of 30,000 cells per well in a 96 well plate and cultured overnight using standard methods. Recombinant purified mature form hBMP-7 was then provided to the cells as a positive control. Cells were also provided with recombinantly expressed hBMP-7 variant protein 3392 eluted from the immunoaffinity column with an acidic buffer or a neutral buffer. hBMP-7 variant protein 3392 was recombinantly expressed in CHO-K1 cells and purified by immunoaffinity chromatography as described above (Example 3). hBMP-7 protein was provided to cells in a quantity sufficient to produce the final concentration indicated in FIG. 4. Cells were then incubated for two days and cell lysates were prepared. Lysates were assayed for alkaline phosphatase activity using standard methods.

Figure 4:
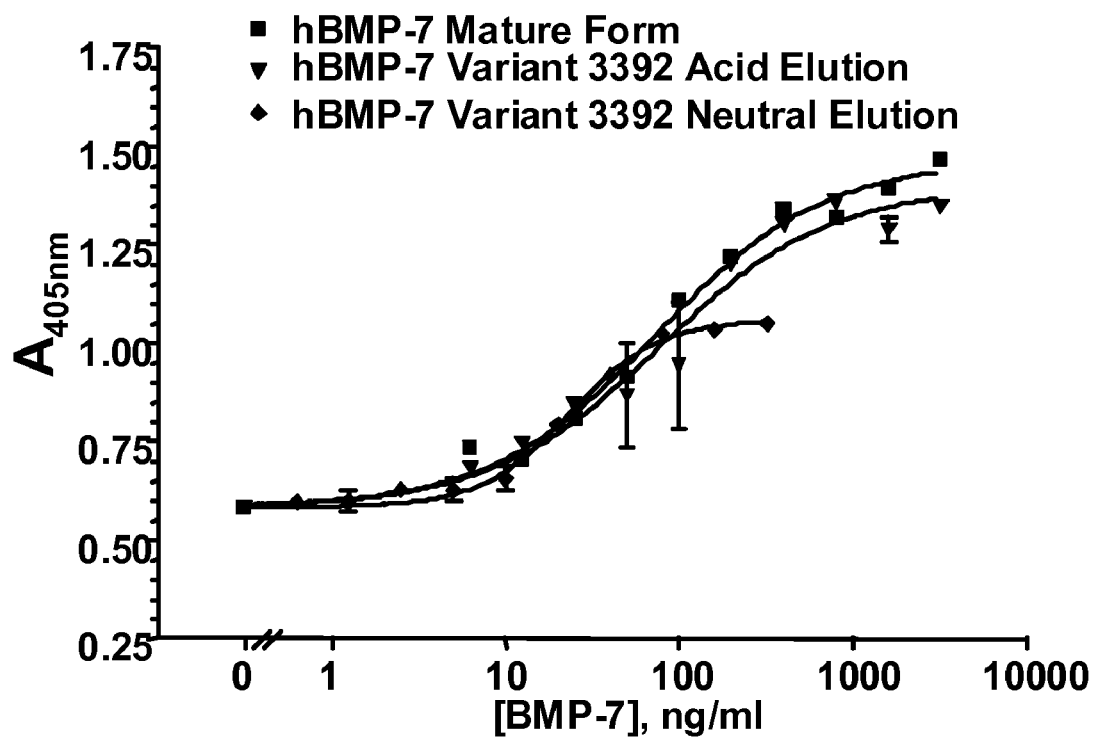
FIG. 4 shows biological activity of hBMP-7 variant 3392 (SEQ ID NO: 42) in a ROS 17/2.8 osteosarcoma cell-based assay system.

These results demonstrate the hBMP-7 variant protein 3392 recombinantly expressed in CHO-K1 cells is biologically active and that this variant protein has biological activity comparable to that of wild-type hBMP-7 provided at an identical concentration (FIG. 4). These results also indicate hBMP-7 variant protein 3392 (SEQ ID NO: 42) will have the ability to induce bone formation through osteogenesis and have utility in the treatment of conditions were inducing bone formation is desirable. Error bars in FIG. 4 represent the mean +/− standard error.

EXAMPLE 5

Biological Activity of hBMP-7 Variant 3392 in a Kidney Cell Proliferation Based Assay System The hBMP-7 variant protein 3392 (SEQ ID NO: 42) is biologically active when recombinantly expressed in CHO-K1 cells (FIG. 4) and assayed in a kidney cell proliferation based assay system. This variant protein also has biological activity comparable to that of wild-type hBMP-7 provided at an identical concentration (FIG. 4).

hBMP-7 mature form biological activity was assayed using a VEPT cell proliferation assay. VEPT cells (ATCC CRL-2087) are a rabbit kidney proximal tubular epithelium derived, immortalized cell line. Biologically active hBMP-7 induces VEPT cell proliferation. Importantly, hBMP-7 has been reported to be an antifibrotic capable of maintaining kidney epithelial cell proliferation and antagonizing the accumulation of extracellular matrix (ECM) in the kidney. Excessive accumulation of extracellular matrix (ECM) in kidney tissues is associated with virtually every type of chronic kidney disease (e.g. renal fibrosis).

VEPT cells were seeded at a density of 2500 cells per well in a 96 well plate and cultured overnight using standard methods. Recombinant purified mature form hBMP-7 was then provided to the cells as a positive control. Cells were also provided with recombinantly expressed hBMP-7 variant protein 3392 eluted from the immunoaffinity column with an acidic buffer or a neutral buffer. hBMP-7 variant protein 3392 was recombinantly expressed in CHO-K1 cells and purified by immunoaffinity chromatography as described above (Example 3). hBMP-7 protein was provided to cells in a quantity sufficient to produced the final concentration indicated in FIG. 5. Cells were then incubated for four days and the CellTiter-Glo® luminescent cell viability assay kit (Promega Inc., Madison, Wis.) was used to detect proliferating cells as directed by the manufacturer.

Figure 5:
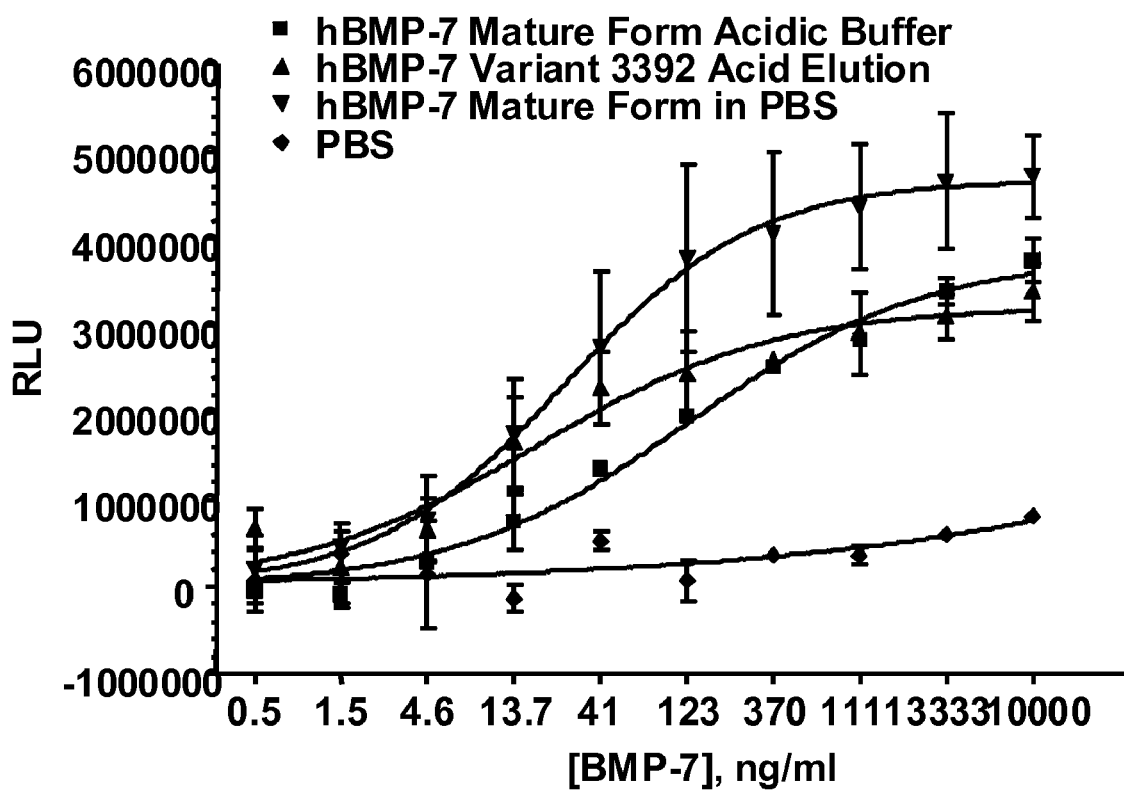
FIG. 5 shows biological activity of hBMP-7 variant 3392 (SEQ ID NO: 42) in a VEPT kidney cell proliferation-based assay system.

These results demonstrate the hBMP-7 variant protein 3392 recombinantly expressed in CHO-K1 cells is biologically active and that this variant protein has biological activity comparable to that of wild-type hBMP-7 provided at an identical concentration (FIG. 5). These results also indicate hBMP-7 variant protein 3392 (SEQ ID NO: 42) will have the ability to induce kidney cell proliferation, antagonize ECM formation and also will have utility in the treatment of kidney disease conditions associated with excessive ECM accumulation. Error bars in FIG. 5 represent the mean +/− standard error.

The present invention now being fully described, it will be apparent to one of ordinary skill in the art that many changes and modifications can be made thereto without departing from the spirit or scope of the appended claims.

SEQUENCE LISTING

```
<160> NUMBER OF SEQ ID NOS: 48

<210> SEQ ID NO 1
<211> LENGTH: 1293
<212> TYPE: DNA
<213> ORGANISM: Homo sapiens

<400> SEQUENCE: 1
atgcacgtgc gctcactgcg agctgcggcg ccgcacagct tcgtggcgct ctgggcaccc      60
ctgttcctgc tgcgctccgc cctggccgac ttcagcctgg acaacgaggt gcactcgagc     120
ttcatccacc ggcgcctccg cagccaggag cggcgggaga tgcagcgcga gatcctctcc     180
attttgggct tgccccaccg cccgcgcccg cacctccagg gcaagcacaa ctcggcaccc     240
atgttcatgc tggacctgta caacgccatg gcggtggagg agggcggcgg gcccggcggc     300
cagggcttct cctaccccta caaggccgtc ttcagtaccc agggcccccc tctggccagc     360
ctgcaagata gccatttcct caccgacgcc gacatggtca tgagcttcgt caacctcgtg     420
gaacatgaca aggaattctt ccaccacgc taccaccatc gagagttccg gtttgatctt      480
tccaagatcc cagaagggga agctgtcacg gcagccgaat tccggatcta caaggactac     540
atccgggaac gcttcgacaa tgagacgttc cggatcagcg tttatcaggt gctccaggag     600
cacttgggca gggaatcgga tctcttcctg ctcgacagcc gtaccctctg ggcctcggag     660
gagggctggc tggtgtttga catcacagcc accagcaacc actgggtggt caatccgcgg     720
cacaacctgg gcctgcagct ctcggtggag acgctggatg ggcagagcat caacccaag      780 ttggcgggcc tgattgggcg gcacgggccc cagaacaagc agcccttcat ggtggctttc     840
ttcaaggcca cggaggtcca cttccgcagc atccggtcca cggggagcaa acagcgcagc     900
cagaaccgct ccaagacgcc caagaaccag gaagccctgc ggatggccaa cgtggcagag     960
```

```
aacagcagca gcgaccagag gcaggcctgt aagaagcacg agctgtatgt cagcttccga   1020
gacctgggct ggcaggactg gatcatcgcg cctgaaggct acgccgccta ctactgtgag   1080
ggggagtgtg ccttccctct gaactcctac atgaacgcca ccaaccacgc catcgtgcag   1140
acgctggtcc acttcatcaa cccggaaacg gtgcccaagc cctgctgtgc gcccacgcag   1200
ctcaatgcca tctccgtcct ctacttcgat gacagctcca acgtcatcct gaagaaatac   1260
agaaacatgg tggtccgggc tgtggctgc cac                                  1293
```

<210> SEQ ID NO 2
<211> LENGTH: 431
<212> TYPE: PRT
<213> ORGANISM: Homo sapiens

<400> SEQUENCE: 2

```
Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
```

```
                305                 310                 315                 320
Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 3
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the R299S and R314S mutations.

<400> SEQUENCE: 3
```

| | | | | | |
|---|---|---|---|---|---|
| atgcacgtgc | gctcactgcg | agctgcggcg | ccgcacagct | tcgtggcgct | ctgggcaccc | 60 |
| ctgttcctgc | tgcgctccgc | cctggccgac | ttcagcctgg | acaacgaggt | gcactcgagc | 120 |
| ttcatccacc | ggcgcctccg | cagccaggag | cggcgggaga | tgcagcgcga | gatcctctcc | 180 |
| attttgggct | tgccccaccg | cccgcgcccg | cacctccagg | gcaagcacaa | ctcggcaccc | 240 |
| atgttcatgc | tggacctgta | caacgccatg | gcggtggagg | agggcggcgg | ccccggcggc | 300 |
| cagggcttct | cctacccctg | caaggccgtc | ttcagtaccc | agggcccccc | tctggccagc | 360 |
| ctgcaagata | gccatttcct | caccgacgcc | gacatggtca | tgagcttcgt | caacctcgtg | 420 |
| gaacatgaca | aggaattctt | ccacccacgc | taccaccatc | gagagttccg | gtttgatctt | 480 |
| tccaagatcc | cagaagggga | agctgtcacg | gcagccgaat | ccggatctac | aaggactac | 540 |
| atccgggaac | gcttcgacaa | tgagacgttc | cggatcagcg | tttatcaggt | gctccaggag | 600 |
| cacttgggca | gggaatcgga | tctcttcctg | ctcgacagcc | gtaccctctg | gcctcggag | 660 |
| gagggctggc | tggtgtttga | catcacagcc | accagcaacc | actgggtggt | caatccgcgg | 720 |
| cacaacctgg | gcctgcagct | ctcggtggag | acgctggatg | ggcagagcat | caaccccaag | 780 |
| ttggcgggcc | tgattggcg | gcacgggccc | cagaacaagc | agcccttcat | ggtggctttc | 840 |
| ttcaaggcca | cggaggtcca | cttccgcagc | atccggtcca | cggggagcaa | acagagcagc | 900 |
| cagaaccgct | ccaagacgcc | caagaaccag | gaagccctga | gcatggccaa | cgtggcagag | 960 |
| aacagcagca | gcgaccagag | gcaggcctgt | aagaagcacg | agctgtatgt | cagcttccga | 1020 |
| gacctgggct | ggcaggactg | gatcatcgcg | cctgaaggct | acgccgccta | ctactgtgag | 1080 |
| ggggagtgtg | ccttccctct | gaactcctac | atgaacgcca | ccaaccacgc | catcgtgcag | 1140 |
| acgctggtcc | acttcatcaa | cccggaaacg | gtgcccaagc | cctgctgtgc | gcccacgcag | 1200 |
| ctcaatgcca | tctccgtcct | ctacttcgat | gacagctcca | acgtcatcct | gaagaaatac | 1260 |
| agaaacatgg | tggtccgggc | tgtggctgc | cac | | | 1293 |

<210> SEQ ID NO 4
<211> LENGTH: 431
<212> TYPE: PRT
<213> ORGANISM: Artificial Sequence
<220> FEATURE:
<223> OTHER INFORMATION: hBMP-7 precursor derived variant peptide chain comprising the R299S and R314S mutations and encoded by a Homo sapiens derived cDNA.

<400> SEQUENCE: 4

```
Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
                35                  40                  45

Gln Glu Arg Arg Glu Met Gln Arg Glu Ile Leu Ser Ile Leu Gly Leu
                50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                    85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
                115                 120                 125

Asp Ala Asp Met Val Met Ser Phe Val Asn Leu Val Glu His Asp Lys
                130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                    165                 170                 175

Tyr Lys Asp Tyr Ile Arg Glu Arg Phe Asp Asn Glu Thr Phe Arg Ile
                180                 185                 190

Ser Val Tyr Gln Val Leu Gln Glu His Leu Gly Arg Glu Ser Asp Leu
                195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                    245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
                275                 280                 285

Arg Ser Ile Arg Ser Thr Gly Ser Lys Gln Ser Ser Gln Asn Arg Ser
                290                 295                 300

Lys Thr Pro Lys Asn Gln Glu Ala Leu Ser Met Ala Asn Val Ala Glu
305                 310                 315                 320

Asn Ser Ser Ser Asp Gln Arg Gln Ala Cys Lys Lys His Glu Leu Tyr
                    325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
```

```
            355                 360                 365
Ser Tyr Met Asn Ala Thr Asn His Ala Ile Val Gln Thr Leu Val His
        370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430

<210> SEQ ID NO 5
<211> LENGTH: 1337
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the ?S293-R299 and R314S mutations.

<400> SEQUENCE: 5
atgcacgtgc gctcactgcg agctgcggcg ccgcacagct tcgtggcgct ctgggcaccc      60
ctgttatgca cgtgcgctca ctgcgagctg cggcgccgca cagcttcgtg gcgctctggg     120 caccctgtt cctgctgcgc tccgccctgg ccgacttcag cctggacaac gaggtgcact     180
cgagcttcat ccaccggcgc ctccgcagcc aggagcggcg ggagatgcag cgcgagatcc     240
tctccatttt gggcttgccc caccgccgc gcccgcacct ccagggcaag cacaactcgg     300
cacccatgtt catgctggac ctgtacaacg ccatggcggt ggaggagggc ggcgggcccg     360
gcggccaggg cttctcctac ccctacaagg ccgtcttcag tacccagggc cccccctctgg   420 ccagcctgca agatagccat ttcctcaccg acgccgacat ggtcatgagc ttcgtcaacc     480
tcgtggaaca tgacaaggaa ttcttccacc cacgctacca ccatcgagag ttccggtttg     540
atctttccaa gatcccagaa ggggaagctg tcacggcagc cgaattccgg atctacaagg     600
actacatccg ggaacgcttc gacaatgaga cgttccggat cagcgtttat caggtgctcc     660
aggagcactt gggcagggaa tcggatctct tcctgctcga cagccgtacc ctctgggcct     720
cggaggaggg ctggctggtg tttgacatca cagccaccag caaccactgg gtggtcaatc     780
cgcggcacaa cctgggcctg cagctctcgg tggagacgct ggatgggcag agcatcaacc     840 ccaagtggc gggcctgatt gggcggcacg gccccagaa caagcagccc ttcatggtgg      900
ctttcttcaa ggccacggag gtccacttcc gcagcatccg gagccagaac cgctccaaga     960
cgcccaagaa ccaggaagcc ctgagcatgg ccaacgtggc agagaacagc agcagcgacc    1020
agaggcaggc ctgtaagaag cacgagctgt atgtcagctt ccgagacctg ggctggcagg    1080
actggatcat cgcgcctgaa ggctacgccg cctactactg tgaggggag tgtgccttcc     1140 ctctgaactc ctacatgaac gccaccaacc acgccatcgt gcagacgctg gtccacttca    1200
tcaacccgga aacggtgccc aagccctgct gtgcgcccac gcagctcaat gccatctccg    1260
tcctctactt cgatgacagc tccaacgtca tcctgaagaa atacagaaac atggtggtcc    1320
gggcctgtgg ctgccac                                                   1337

<210> SEQ ID NO 6
<211> LENGTH: 424
<212> TYPE: PRT
<213> ORGANISM: Artificial Sequence
<220> FEATURE:
<223> OTHER INFORMATION: hBMP-7 precursor derived variant peptide chain
``` comprising the ?S293-R299 and R314S mutations and
encoded by a Homo sapiens derived cDNA.

<400> SEQUENCE: 6

```
Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
                35                  40                  45

Gln Glu Arg Arg Glu Met Gln Arg Glu Ile Leu Ser Ile Leu Gly Leu
 50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
                115                 120                 125

Asp Ala Asp Met Val Met Ser Phe Val Asn Leu Val Glu His Asp Lys
 130                 135                 140

Glu Phe Phe His Pro Arg Tyr His His Arg Glu Phe Arg Phe Asp Leu
145                  150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
                180                 185                 190

Ser Val Tyr Gln Val Leu Gln Glu His Leu Gly Arg Glu Ser Asp Leu
                195                 200                 205

Phe Leu Leu Asp Ser Arg Thr Leu Trp Ala Ser Glu Glu Gly Trp Leu
 210                 215                 220

Val Phe Asp Ile Thr Ala Thr Ser Asn His Trp Val Val Asn Pro Arg
225                  230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
                275                 280                 285

Arg Ser Ile Arg Ser Gln Asn Arg Ser Lys Thr Pro Lys Asn Gln Glu
290                  295                 300

Ala Leu Ser Met Ala Asn Val Ala Glu Asn Ser Ser Ser Asp Gln Arg
305                  310                 315                 320

Gln Ala Cys Lys Lys His Glu Leu Tyr Val Ser Phe Arg Asp Leu Gly
                325                 330                 335

Trp Gln Asp Trp Ile Ile Ala Pro Glu Gly Tyr Ala Ala Tyr Tyr Cys
                340                 345                 350

Glu Gly Glu Cys Ala Phe Pro Leu Asn Ser Tyr Met Asn Ala Thr Asn
                355                 360                 365

His Ala Ile Val Gln Thr Leu Val His Phe Ile Asn Pro Glu Thr Val
 370                 375                 380

Pro Lys Pro Cys Cys Ala Pro Thr Gln Leu Asn Ala Ile Ser Val Leu
385                  390                 395                 400
```

Tyr Phe Asp Asp Ser Ser Asn Val Ile Leu Lys Lys Tyr Arg Asn Met
                405                 410                 415

Val Val Arg Ala Cys Gly Cys His
            420

<210> SEQ ID NO 7
<211> LENGTH: 1227
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the ?S293-M314 mutation.

<400> SEQUENCE: 7
atgcacgtgc gctcactgcg agctgcggcg ccgcacagct tcgtggcgct ctgggcaccc      60
ctgttcctgc tgcgctccgc cctggccgac ttcagcctgg acaacgaggt gcactcgagc     120
ttcatccacc ggcgcctccg cagccaggag cggcgggaga tgcagcgcga gatcctctcc     180
attttgggct tgccccaccg cccgcgcccc cacctccagg gcaagcacaa ctcggcaccc     240
atgttcatgc tggacctgta caacgccatg gcggtggagg agggcggcgg gcccggcggc     300
cagggcttct cctaccccta caaggccgtc ttcagtaccc agggcccccc tctggccagc     360
ctgcaagata gccatttcct caccgacgcc gacatggtca tgagcttcgt caacctcgtg     420
gaacatgaca aggaattctt ccacccacgc taccaccatc gagagttccg gtttgatctt     480
tccaagatcc cagaagggga agctgtcacg gcagccgaat ccggatctaa caggactac      540 atccgggaac gcttcgacaa tgagacgttc cggatcagcg tttatcaggt gctccaggag     600
cacttgggca gggaatcgga tctcttcctg ctcgacagcc gtaccctctg gcctcggag      660 gagggctggc tggtgtttga catcacagcc accagcaacc actgggtggt caatccgcgg     720
cacaacctgg gcctgcagct ctcggtggag acgctggatg ggcagagcat caaccccaag     780
ttggcgggcc tgattgggcg gcacgggccc cagaacaagc agcccttcat ggtggctttc     840
ttcaaggcca cggaggtcca cttccgcagc atccggatgg ccaacgtggc agagaacagc     900
agcagcgacc agaggcaggc ctgtaagaag cacgagctgt atgtcagctt ccgagacctg     960
ggctggcagg actggatcat cgcgcctgaa ggctacgccg cctactactg tgaggggag     1020 tgtgccttcc ctctgaactc ctacatgaac gccaccaacc acgccatcgt gcagacgctg    1080
gtccacttca tcaacccgga aacggtgccc aagccctgct gtgcgcccac gcagctcaat    1140
gccatctccg tcctctactt cgatgacagc tccaacgtca tcctgaagaa atacagaaac    1200
atggtggtcc gggcctgtgg ctgccac                                       1227

<210> SEQ ID NO 8
<211> LENGTH: 409
<212> TYPE: PRT
<213> ORGANISM: Artificial Sequence
<220> FEATURE:
<223> OTHER INFORMATION: hBMP-7 precursor derived variant peptide chain
      comprising the ?S293-M314 mutation and encoded by
      a Homo sapiens derived cDNA.

<400> SEQUENCE: 8

Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
            20                  25                  30

```
Leu Asp Asn Glu Val His Ser Ser Phe Ile His Arg Arg Leu Arg Ser
             35                  40                  45

Gln Glu Arg Arg Glu Met Gln Arg Glu Ile Leu Ser Ile Leu Gly Leu
 50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
            210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
            275                 280                 285

Arg Ser Ile Arg Met Ala Asn Val Ala Glu Asn Ser Ser Ser Asp Gln
290                 295                 300

Arg Gln Ala Cys Lys Lys His Glu Leu Tyr Val Ser Phe Arg Asp Leu
305                 310                 315                 320

Gly Trp Gln Asp Trp Ile Ile Ala Pro Glu Gly Tyr Ala Ala Tyr Tyr
                325                 330                 335

Cys Glu Gly Glu Cys Ala Phe Pro Leu Asn Ser Tyr Met Asn Ala Thr
            340                 345                 350

Asn His Ala Ile Val Gln Thr Leu Val His Phe Ile Asn Pro Glu Thr
            355                 360                 365

Val Pro Lys Pro Cys Cys Ala Pro Thr Gln Leu Asn Ala Ile Ser Val
            370                 375                 380

Leu Tyr Phe Asp Asp Ser Ser Asn Val Ile Leu Lys Lys Tyr Arg Asn
385                 390                 395                 400

Met Val Val Arg Ala Cys Gly Cys His
                405
```

<210> SEQ ID NO 9
<211> LENGTH: 1224
<212> TYPE: DNA
<213> ORGANISM: Artificial Sequence
<220> FEATURE:
<223> OTHER INFORMATION: Homo sapiens derived cDNA encoding a hBMP-7

-continued precursor derived variant peptide chain comprising the ?S293-M315 mutation.

<400> SEQUENCE: 9

```
atgcacgtgc gctcactgcg agctgcggcg ccgcacagct tcgtggcgct ctgggcaccc      60
ctgttcctgc tgcgctccgc cctggccgac ttcagcctgg acaacgaggt gcactcgagc     120
ttcatccacc ggcgcctccg cagccaggag cggcgggaga tgcagcgcga gatcctctcc     180
attttgggct gccccaccg cccgcgcccg cacctccagg gcaagcacaa ctcggcaccc      240
atgttcatgc tggacctgta caacgccatg gcggtggagg agggcggcgg gcccggcggc     300
cagggcttct cctacccta caaggccgtc ttcagtaccc agggcccccc tctggccagc     360
ctgcaagata gccatttcct caccgacgcc gacatggtca tgagcttcgt caacctcgtg     420
gaacatgaca aggaattctt ccacccacgc taccaccatc gagagttccg gtttgatctt     480
tccaagatcc cagaagggga agctgtcacg gcagccgaat ccggatcta caaggactac     540
atccgggaac gcttcgacaa tgagacgttc cggatcagcg tttatcaggt gctccaggag     600
cacttgggca gggaatcgga tctcttcctg ctcgacagcc gtaccctctg gcctcggag      660
gagggctggc tggtgtttga catcacagcc accagcaacc actgggtggt caatccgcgg     720
cacaacctgg gcctgcagct ctcggtggag acgctggatg gcagagcat caaccccaag      780
ttggcgggcc tgattgggcg cacgggccc cagaacaagc agcccttcat ggtggctttc      840
ttcaaggcca cggaggtcca cttccgcagc atcggggcca acgtggcaga aacagcagc      900
agcgaccaga ggcaggcctg taagaagcac gagctgtatg tcagcttccg agacctgggc     960
tggcaggact ggatcatcgc gcctgaaggc tacgccgcct actactgtga gggggagtgt    1020
gccttccctc tgaactccta catgaacgcc accaaccacg ccatcgtgca gacgctggtc    1080
cacttcatca acccggaaac ggtgcccaag ccctgctgtg cgcccacgca gctcaatgcc    1140
atctccgtcc tctacttcga tgacagctcc aacgtcatcc tgaagaaata cagaaacatg    1200
gtggtccggg cctgtggctg ccac                                           1224
```

<210> SEQ ID NO 10
<211> LENGTH: 408
<212> TYPE: PRT
<213> ORGANISM: Artificial Sequence
<220> FEATURE:
<223> OTHER INFORMATION: hBMP-7 precursor derived variant peptide chain comprising the ?S293-M315 mutation and encoded by a Homo sapiens derived cDNA.

<400> SEQUENCE: 10

```
Met His Val Arg Ser Leu Arg Ala Ala Ala Pro His Ser Phe Val Ala
  1               5                  10                  15

Leu Trp Ala Pro Leu Phe Leu Leu Arg Ser Ala Leu Ala Asp Phe Ser
             20                  25                  30

Leu Asp Asn Glu Val His Ser Ser Phe Ile His Arg Arg Leu Arg Ser
         35                  40                  45

Gln Glu Arg Arg Glu Met Gln Arg Glu Ile Leu Ser Ile Leu Gly Leu
     50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
            100                 105                 110
```

-continued

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ala Asn Val Ala Glu Asn Ser Ser Ser Asp Gln Arg
    290                 295                 300

Gln Ala Cys Lys Lys His Glu Leu Tyr Val Ser Phe Arg Asp Leu Gly
305                 310                 315                 320

Trp Gln Asp Trp Ile Ile Ala Pro Glu Gly Tyr Ala Ala Tyr Tyr Cys
                325                 330                 335

Glu Gly Glu Cys Ala Phe Pro Leu Asn Ser Tyr Met Asn Ala Thr Asn
            340                 345                 350

His Ala Ile Val Gln Thr Leu Val His Phe Ile Asn Pro Glu Thr Val
        355                 360                 365

Pro Lys Pro Cys Cys Ala Pro Thr Gln Leu Asn Ala Ile Ser Val Leu
    370                 375                 380

Tyr Phe Asp Asp Ser Ser Asn Val Ile Leu Lys Lys Tyr Arg Asn Met
385                 390                 395                 400

Val Val Arg Ala Cys Gly Cys His
                405

<210> SEQ ID NO 11
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the R299S, R314S, and L407K mutations.

<400> SEQUENCE: 11
atgcacgtgc gctcactgcg agctgcggcg ccgcacagct tcgtggcgct ctgggcaccc     60
ctgttcctgc tgcgctccgc cctggccgac ttcagcctgg acaacgaggt gcactcgagc    120
ttcatccacc ggcgcctccg cagccaggag cggcgggaga tgcagcgcga gatcctctcc    180
attttgggct gccccaccg cccgcgcccg cacctccagg gcaagcacaa ctcggcaccc    240
atgttcatgc tggacctgta caacgccatg gcggtggagg agggcggcgg gcccggcggc    300

```
caggcttct cctaccccta caaggccgtc ttcagtaccc agggcccccc tctggccagc    360
ctgcaagata gccatttcct caccgacgcc gacatggtca tgagcttcgt caacctcgtg    420
gaacatgaca aggaattctt ccacccacgc taccaccatc gagagttccg gtttgatctt    480
tccaagatcc agaagggga agctgtcacg gcagccgaat tccggatcta caaggactac    540
atccgggaac gcttcgacaa tgagacgttc cggatcagcg tttatcaggt gctccaggag    600
cacttgggca gggaatcgga tctcttcctg ctcgacagcc gtaccctctg gcctcggag    660 gagggctggc tggtgtttga catcacagcc accagcaacc actgggtggt caatccgcgg    720
cacaacctgg gcctgcagct ctcggtggag acgctggatg gcagagcat caaccccaag    780 ttggcgggcc tgattgggcg cacgggccc cagaacaagc agcccttcat ggtggctttc    840
ttcaaggcca cggaggtcca cttccgcagc atccggtcca cggggagcaa acagagcagc    900
cagaaccgct ccaagacgcc caagaaccag gaagccctga gcatggccaa cgtggcagag    960
aacagcagca gcgaccagag gcaggcctgt aagaagcacg agctgtatgt cagcttccga    1020
gacctgggct ggcaggactg gatcatcgcg cctgaaggct acgccgccta ctactgtgag    1080
ggggagtgtg ccttccctct gaactcctac atgaacgcca ccaaccacgc catcgtgcag    1140
acgctggtcc acttcatcaa cccggaaacg gtgcccaagc cctgctgtgc gcccacgcag    1200
ctcaatgcca tctccgtcaa gtacttcgat gacagctcca cgtcatcct gaagaaatac    1260 agaaacatgg tggtccgggc ctgtggctgc cac                                 1293
```

<210> SEQ ID NO 12
<211> LENGTH: 431
<212> TYPE: PRT
<213> ORGANISM: Artificial Sequence
<220> FEATURE:
<223> OTHER INFORMATION: hBMP-7 precursor derived variant peptide chain
      comprising the R299S, R314S, and L407K mutations
      and encoded by a Homo sapiens derived cDNA.

<400> SEQUENCE: 12

```
Met His Val Arg Ser Leu Arg Ala Ala Ala Pro His Ser Phe Val Ala
  1               5                  10                  15

Leu Trp Ala Pro Leu Phe Leu Leu Arg Ser Ala Leu Ala Asp Phe Ser
             20                  25                  30

Leu Asp Asn Glu Val His Ser Ser Phe Ile His Arg Arg Leu Arg Ser
         35                  40                  45

Gln Glu Arg Arg Glu Met Gln Arg Glu Ile Leu Ser Ile Leu Gly Leu
     50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175
```

```
Tyr Lys Asp Tyr Ile Arg Glu Arg Phe Asp Asn Glu Thr Phe Arg Ile
            180                 185                 190
Ser Val Tyr Gln Val Leu Gln Glu His Leu Gly Arg Glu Ser Asp Leu
        195                 200                 205
Phe Leu Leu Asp Ser Arg Thr Leu Trp Ala Ser Glu Glu Gly Trp Leu
    210                 215                 220
Val Phe Asp Ile Thr Ala Thr Ser Asn His Trp Val Val Asn Pro Arg
225                 230                 235                 240
His Asn Leu Gly Leu Gln Leu Ser Val Glu Thr Leu Asp Gly Gln Ser
                245                 250                 255
Ile Asn Pro Lys Leu Ala Gly Leu Ile Gly Arg His Gly Pro Gln Asn
            260                 265                 270
Lys Gln Pro Phe Met Val Ala Phe Phe Lys Ala Thr Glu Val His Phe
        275                 280                 285
Arg Ser Ile Arg Ser Thr Gly Ser Lys Gln Ser Ser Gln Asn Arg Ser
    290                 295                 300
Lys Thr Pro Lys Asn Gln Glu Ala Leu Ser Met Ala Asn Val Ala Glu
305                 310                 315                 320
Asn Ser Ser Asp Gln Arg Gln Ala Cys Lys Lys His Glu Leu Tyr
                325                 330                 335
Val Ser Phe Arg Asp Leu Gly Trp Gln Asp Trp Ile Ile Ala Pro Glu
            340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Val His
    370                 375                 380
Phe Ile Asn Pro Glu Thr Val Pro Lys Pro Cys Cys Ala Pro Thr Gln
385                 390                 395                 400
Leu Asn Ala Ile Ser Val Lys Tyr Phe Asp Asp Ser Ser Asn Val Ile
                405                 410                 415
Leu Lys Lys Tyr Arg Asn Met Val Val Arg Ala Cys Gly Cys His
            420                 425                 430

<210> SEQ ID NO 13
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the R299S, R314S, and F409K mutations.

<400> SEQUENCE: 13
atgcacgtgc gctcactgcg agctgcggcg ccgcacagct tcgtggcgct ctgggcaccc      60
ctgttcctgc tgcgctccgc cctggccgac ttcagcctgg acaacgaggt gcactcgagc     120
ttcatccacc ggcgcctccg cagccaggag cggcgggaga tgcagcgcga gatcctctcc     180
attttgggct tgccccaccg cccgcgcccg cacctccagg gcaagcacaa ctcggcaccc     240
atgttcatgc tggacctgta caacgccatg gcggtggagg agggcggcgg gcccggcggc     300
cagggcttct cctacccct caaggccgtc ttcagtaccc agggccccc tctggccagc     360 ctgcaagata gccatttcct caccgacgcc gacatggtca tgagcttcgt caacctcgtg     420
gaacatgaca aggaattctt ccacccacgc taccaccatc gagagttccg gtttgatctt     480
tccaagatcc agaaggggga agctgtcacg gcagccgaat ccggatcta caaggactac     540
```

-continued

```
atccgggaac gcttcgacaa tgagacgttc cggatcagcg tttatcaggt gctccaggag    600
cacttgggca gggaatcgga tctcttcctg ctcgacagcc gtaccctctg ggcctcggag    660
gagggctggc tggtgtttga catcacagcc accagcaacc actgggtggt caatccgcgg    720
cacaacctgg gcctgcagct ctcggtggag acgctggatg gcagagcat caaccccaag    780 ttggcgggcc tgattgggcg cacgggccc cagaacaagc agcccttcat ggtggctttc    840
ttcaaggcca cggaggtcca cttccgcagc atccggtcca cggggagcaa acagagcagc    900
cagaaccgct ccaagacgcc caagaaccag gaagccctga gcatggccaa cgtggcagag    960
aacagcagca gcgaccagag gcaggcctgt aagaagcacg agctgtatgt cagcttccga    1020
gacctgggct ggcaggactg gatcatcgcg cctgaaggct acgccgccta ctactgtgag    1080
ggggagtgtg ccttccctct gaactcctac atgaacgcca ccaaccacgc catcgtgcag    1140
acgctggtcc acttcatcaa cccggaaacg gtgcccaagc cctgctgtgc gcccacgcag    1200
ctcaatgcca tctccgtcct ctacaaggat gacagctcca acgtcatcct gaagaaatac    1260
agaaacatgg tggtccgggc ctgtggctgc cac                                  1293
```

<210> SEQ ID NO 14
<211> LENGTH: 431
<212> TYPE: PRT
<213> ORGANISM: Artificial Sequence
<220> FEATURE:
<223> OTHER INFORMATION: hBMP-7 precursor derived variant peptide chain
      comprising the R299S, R314S, and F409K mutations
      and encoded by a Homo sapiens derived cDNA.

<400> SEQUENCE: 14

```
Met His Val Arg Ser Leu Arg Ala Ala Ala Pro His Ser Phe Val Ala
  1               5                  10                  15

Leu Trp Ala Pro Leu Phe Leu Leu Arg Ser Ala Leu Ala Asp Phe Ser
             20                  25                  30

Leu Asp Asn Glu Val His Ser Ser Phe Ile His Arg Arg Leu Arg Ser
         35                  40                  45

Gln Glu Arg Arg Glu Met Gln Arg Glu Ile Leu Ser Ile Leu Gly Leu
     50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220
```

```
Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
            245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Ser Ser Gln Asn Arg Ser
290                 295                 300

Lys Thr Pro Lys Asn Gln Glu Ala Leu Ser Met Ala Asn Val Ala Glu
305                 310                 315                 320

Asn Ser Ser Ser Asp Gln Arg Gln Ala Cys Lys Lys His Glu Leu Tyr
            325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
            370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Lys Asp Asp Ser Ser Asn Val Ile
            405                 410                 415

Leu Lys Lys Tyr Arg Asn Met Val Val Arg Ala Cys Gly Cys His
            420                 425                 430

<210> SEQ ID NO 15
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the R299S, R314S, and L417R mutations.

<400> SEQUENCE: 15
atgcacgtgc gctcactgcg agctgcggcg ccgcacagct tcgtggcgct ctgggcaccc      60
ctgttcctgc tgcgctccgc cctggccgac ttcagcctgg acaacgaggt gcactcgagc    120
ttcatccacc ggcgcctccg cagccaggag cggcgggaga tgcagcgcga gatcctctcc    180
attttgggct tgccccaccg cccgcgcccg cacctccagg gcaagcacaa ctcggcaccc    240
atgttcatgc tggacctgta caacgccatg gcggtggagg agggcggcgg gcccggcggc    300
cagggcttct cctaccccta caaggccgtc ttcagtaccc agggccccccc tctggccagc    360 ctgcaagata gccatttcct caccgacgcc gacatggtca tgagcttcgt caacctcgtg    420
gaacatgaca aggaattctt ccacccacgc taccaccatc gagagttccg gtttgatctt    480
tccaagatcc cagaagggga agctgtcacg gcagccgaat ccggatctca aggactac      540 atccgggaac gcttcgacaa tgagacgttc cggatcagcg tttatcaggt gctccaggag    600
cacttgggca gggaatcgga tctcttcctg ctcgacagcc gtaccctctg ggcctcggag    660
gagggctggc tggtgtttga catcacagcc accagcaacc actgggtggt caatccgcgg    720
cacaacctgg gcctgcagct ctcggtggag acgctggatg gcagagcat caaccccaag    780 ttggcgggcc tgattggcg gcacgggccc cagaacaagc agcccttcat ggtggctttc    840
```

```
ttcaaggcca cggaggtcca cttccgcagc atccggtcca cggggagcaa acagagcagc    900
cagaaccgct ccaagacgcc caagaaccag gaagccctga gcatggccaa cgtggcagag    960
aacagcagca gcgaccagag gcaggcctgt aagaagcacg agctgtatgt cagcttccga   1020
gacctgggct ggcaggactg gatcatcgcg cctgaaggct acgccgccta ctactgtgag   1080
ggggagtgtg ccttccctct gaactcctac atgaacgcca ccaaccacgc catcgtgcag   1140
acgctggtcc acttcatcaa cccggaaacg gtgcccaagc cctgctgtgc gcccacgcag   1200
ctcaatgcca tctccgtcct ctacttcgat gacagctcca acgtcatccg gaagaaatac   1260
agaaacatgg tggtccgggc ctgtggctgc cac                                1293
```

<210> SEQ ID NO 16
<211> LENGTH: 431
<212> TYPE: PRT
<213> ORGANISM: Artificial Sequence
<220> FEATURE:
<223> OTHER INFORMATION: hBMP-7 precursor derived variant peptide chain
      comprising the R299S, R314S, and L417R mutations
      and encoded by a Homo sapiens derived cDNA.

<400> SEQUENCE: 16

```
Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270
```

```
Lys Gln Pro Phe Met Val Ala Phe Lys Ala Thr Glu Val His Phe
        275                 280                 285
Arg Ser Ile Arg Ser Thr Gly Ser Lys Gln Ser Ser Gln Asn Arg Ser
    290                 295                 300
Lys Thr Pro Lys Asn Gln Glu Ala Leu Ser Met Ala Asn Val Ala Glu
305                 310                 315                 320
Asn Ser Ser Ser Asp Gln Arg Gln Ala Cys Lys Lys His Glu Leu Tyr
                325                 330                 335
Val Ser Phe Arg Asp Leu Gly Trp Gln Asp Trp Ile Ile Ala Pro Glu
            340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Val His
    370                 375                 380
Phe Ile Asn Pro Glu Thr Val Pro Lys Pro Cys Cys Ala Pro Thr Gln
385                 390                 395                 400
Leu Asn Ala Ile Ser Val Leu Tyr Phe Asp Asp Ser Ser Asn Val Ile
                405                 410                 415
Arg Lys Lys Tyr Arg Asn Met Val Val Arg Ala Cys Gly Cys His
            420                 425                 430

<210> SEQ ID NO 17
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the R299S, R314S, and L382K mutations.

<400> SEQUENCE: 17
atgcacgtgc gctcactgcg agctgcggcg ccgcacagct tcgtggcgct ctgggcaccc       60
ctgttcctgc tgcgctccgc cctggccgac ttcagcctgg acaacgaggt gcactcgagc      120
ttcatccacc ggcgcctccg cagccaggag cggcgggaga tgcagcgcga gatcctctcc      180
attttgggct gccccaccg cccgcgcccg cacctccagg caagcacaa ctcggcaccc        240 atgttcatgc tggacctgta caacgccatg gcggtggagg agggcggcgg gcccggcggc      300
cagggcttct cctacccta caaggccgtc ttcagtaccc agggcccccc tctggccagc      360
ctgcaagata gccatttcct caccgacgcc gacatggtca tgagcttcgt caacctcgtg      420
gaacatgaca aggaattctt ccacccacgc taccaccatc gagagttccg gtttgatctt      480
tccaagatcc cagaagggga agctgtcacg gcagccgaat ccggatctc aaggactac        540 atccgggaac gcttcgacaa tgagacgttc cggatcagcg tttatcaggt gctccaggag      600
cacttgggca gggaatcgga tctcttcctg ctcgacagcc gtaccctctg gcctcggag       660 gagggctggc tggtgtttga catcacagcc accagcaacc actgggtggt caatccgcgg      720
cacaacctgg gcctgcagct ctcggtggag acgctggatg gcagagcat caaccccaag       780 ttggcgggcc tgattggcg gcacgggccc cagaacaagc agcccttcat ggtggctttc       840
ttcaaggcca cggaggtcca cttccgcagc atccggtcca cggggagcaa acagagcagc      900
cagaaccgct ccaagacgcc caagaaccag gaagccctga gcatggccaa cgtggcagag      960
aacagcagca cgaccagag gcaggcctgt aagaagcacg agctgtatgt cagcttccga     1020
gacctgggct ggcaggactg gatcatcgcg cctgaaggct acgccgccta ctactgtgag     1080
```

```
ggggagtgtg ccttccctct gaactcctac atgaacgcca ccaaccacgc catcgtgcag    1140
acgaaggtcc acttcatcaa cccggaaacg gtgcccaagc cctgctgtgc gcccacgcag    1200
ctcaatgcca tctccgtcct ctacttcgat gacagctcca acgtcatcct gaagaaatac    1260
agaaacatgg tggtccgggc tgtggctgc cac                                  1293
```

<210> SEQ ID NO 18
<211> LENGTH: 431
<212> TYPE: PRT
<213> ORGANISM: Artificial Sequence
<220> FEATURE:
<223> OTHER INFORMATION: hBMP-7 precursor derived variant peptide chain
      comprising the R299S, R314S, and L382K mutations
      and encoded by a Homo sapiens derived cDNA.

<400> SEQUENCE: 18

```
Met His Val Arg Ser Leu Arg Ala Ala Ala Pro His Ser Phe Val Ala
  1               5                  10                  15

Leu Trp Ala Pro Leu Phe Leu Leu Arg Ser Ala Leu Ala Asp Phe Ser
             20                  25                  30

Leu Asp Asn Glu Val His Ser Ser Phe Ile His Arg Arg Leu Arg Ser
         35                  40                  45

Gln Glu Arg Arg Glu Met Gln Arg Glu Ile Leu Ser Ile Leu Gly Leu
     50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Ser Ser Gln Asn Arg Ser
    290                 295                 300

Lys Thr Pro Lys Asn Gln Glu Ala Leu Ser Met Ala Asn Val Ala Glu
305                 310                 315                 320
```

```
Asn Ser Ser Ser Asp Gln Arg Gln Ala Cys Lys Lys His Glu Leu Tyr
            325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Lys Val His
            370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
            405                 410                 415

Leu Lys Lys Tyr Arg Asn Met Val Val Arg Ala Cys Gly Cys His
            420                 425                 430

<210> SEQ ID NO 19
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the R299S, R314S, and L382N mutations.

<400> SEQUENCE: 19
atgcacgtgc gctcactgcg agctgcggcg ccgcacagct tcgtggcgct ctgggcaccc      60
ctgttcctgc tgcgctccgc cctggccgac ttcagcctgg acaacgaggt gcactcgagc     120
ttcatccacc ggcgcctccg cagccaggag cggcgggaga tgcagcgcga gatcctctcc     180
attttgggct gccccaccg cccgcgcccg cacctccagg gcaagcacaa ctcggcaccc     240
atgttcatgc tggacctgta caacgccatg gcggtggagg agggcggcgg gcccggcggc     300
cagggcttct cctaccccta caaggccgtc ttcagtaccc agggcccccc tctggccagc     360
ctgcaagata gccatttcct caccgacgcc gacatggtca tgagcttcgt caacctcgtg     420
gaacatgaca aggaattctt ccacccacgc taccaccatc gagagttccg gtttgatctt     480
tccaagatcc agaaggggga agctgtcacg gcagccgaat ccggatcta caaggactac     540 atccgggaac gcttcgacaa tgagacgttc cggatcagcg tttatcaggt gctccaggag     600
cacttgggca gggaatcgga tctcttcctg ctcgacagcc gtaccctctg ggcctcggag     660
gagggctggc tggtgtttga catcacagcc accagcaacc actgggtggt caatccgcgg     720
cacaacctgg cctgcagct ctcggtggag acgctggatg ggcagagcat caaccccaag     780
ttggcgggcc tgattgggcg cacgggccc agaacaagc agccccttcat ggtggctttc     840 ttcaaggcca cggaggtcca cttccgcagc atccggtcca cggggagcaa acagagcagc     900
cagaaccgct ccaagacgcc caagaaccag aagccctga gcatggccaa cgtggcagag     960
aacagcagca cgaccagag gcaggcctgt aagaagcacg agctgtatgt cagcttccga    1020
gacctgggct ggcaggactg gatcatcgcg cctgaaggct acgccgccta ctactgtgag    1080
ggggagtgtg ccttccctct gaactcctac atgaacgcca ccaaccacgc catcgtgcag    1140
acgaacgtcc acttcatcaa cccggaaacg gtgcccaagc cctgctgtgc cccacgcag    1200 ctcaatgcca tctccgtcct ctacttcgat gacagctcca acgtcatcct gaagaaatac    1260
agaaacatgg tggtccgggc ctgtggctgc cac                                 1293
```

```
<210> SEQ ID NO 20
<211> LENGTH: 431
<212> TYPE: PRT
<213> ORGANISM: Artificial Sequence
<220> FEATURE:
<223> OTHER INFORMATION: hBMP-7 precursor derived variant peptide chain
      comprising the R299S, R314S, and L382N mutations
      and encoded by a Homo sapiens derived cDNA.

<400> SEQUENCE: 20

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Ser Ser Gln Asn Arg Ser
290                 295                 300

Lys Thr Pro Lys Asn Gln Glu Ala Leu Ser Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365
```

```
Ser Tyr Met Asn Ala Thr Asn His Ala Ile Val Gln Thr Asn Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
            405                 410                 415

Leu Lys Lys Tyr Arg Asn Met Val Val Arg Ala Cys Gly Cys His
        420                 425                 430

<210> SEQ ID NO 21
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the R299S, R314S, and V383K mutations.

<400> SEQUENCE: 21
atgcacgtgc gctcactgcg agctgcggcg ccgcacagct tcgtggcgct ctgggcaccc        60
ctgttcctgc tgcgctccgc cctggccgac ttcagcctgg acaacgaggt gcactcgagc       120
ttcatccacc ggcgcctccg cagccaggag cggcgggaga tgcagcgcga gatcctctcc       180
attttgggct tgccccaccg cccgcgcccg cacctccagg gcaagcacaa ctcggcaccc       240
atgttcatgc tggacctgta caacgccatg gcggtggagg agggcggcgg gcccggcggc       300
cagggcttct cctaccccta caaggccgtc ttcagtaccc agggccccccc tctggccagc       360 ctgcaagata gccatttcct caccgacgcc gacatggtca tgagcttcgt caacctcgtg       420
gaacatgaca aggaattctt ccacccacgc taccaccatc gagagttccg gtttgatctt       480
tccaagatcc cagaagggga agctgtcacg gcagccgaat tccggatcta caaggactac       540
atccgggaac gcttcgacaa tgagacgttc cggatcagcg tttatcaggt gctccaggag       600
cacttgggca gggaatcgga tctcttcctg ctcgacagcc gtaccctctg ggcctcggag       660
gagggctggc tggtgtttga catcacagcc accagcaacc actgggtggt caatccgcgg       720
cacaacctgg gcctgcagct ctcggtggag acgctggatg gcagagcat caaccccaag       780 ttggcgggcc tgattgggcg cacgggccc agaacaagc agcccttcat ggtggctttc       840
ttcaaggcca cggaggtcca cttccgcagc atccggtcca cggggagcaa acagagcagc       900
cagaaccgct ccaagacgcc caagaaccag gaagccctga gcatggccaa cgtggcagag       960
aacagcagca gcgaccagag gcaggcctgt aagaagcacg agctgtatgt cagcttccga      1020
gacctgggct ggcaggactg gatcatcgcg cctgaaggct acgccgccta ctactgtgag      1080
ggggagtgtg ccttccctct gaactcctac atgaacgcca ccaaccacgc catcgtgcag      1140
acgctgaagc acttcatcaa cccggaaacg gtgcccaagc cctgctgtgc gcccacgcag      1200
ctcaatgcca tctccgtcct ctacttcgat gacagctcca acgtcatcct gaagaaatac      1260
agaaacatgg tggtccgggc ctgtggctgc cac                                     1293

<210> SEQ ID NO 22
<211> LENGTH: 431
<212> TYPE: PRT
<213> ORGANISM: Artificial Sequence
<220> FEATURE:
<223> OTHER INFORMATION: hBMP-7 precursor derived variant peptide chain
      comprising the R299S, R314S, and V383K mutations
      and encoded by a Homo sapiens derived cDNA.
```

<400> SEQUENCE: 22

```
Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
 50                  55                  60

Pro His Arg Pro Arg Pro His Leu Gln Gly Lys His Asn Ser Ala Pro
65                   70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
            130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Ser Gln Asn Arg Ser
            290                 295                 300

Lys Thr Pro Lys Asn Gln Glu Ala Leu Ser Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Lys His
            370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415
```

Leu Lys Lys Tyr Arg Asn Met Val Val Arg Ala Cys Gly Cys His
            420                 425                 430

<210> SEQ ID NO 23
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the R299S, R314S, and I386R mutations.

<400> SEQUENCE: 23

```
atgcacgtgc gctcactgcg agctgcggcg ccgcacagct tcgtggcgct ctgggcaccc      60
ctgttcctgc tgcgctccgc cctggccgac ttcagcctgg acaacgaggt gcactcgagc     120
ttcatccacc ggcgcctccg cagccaggag cggcgggaga tgcagcgcga tcctctcc      180
attttgggct tgccccaccg cccgcgcccg cacctccagg caagcacaa ctcggcaccc     240
atgttcatgc tggacctgta caacgccatg gcggtggagg agggcggcgg gccccggcggc   300
cagggcttct cctaccccta caaggccgtc ttcagtaccc agggcccccc tctggccagc    360
ctgcaagata gccatttcct caccgacgcc gacatggtca tgagcttcgt caacctcgtg    420
gaacatgaca aggaattctt ccacccacgc taccaccatc gagagttccg gtttgatctt    480
tccaagatcc agaagggga agctgtcacg gcagccgaat tccggatcta aaggactac     540
atccgggaac gcttcgacaa tgagacgttc cggatcagcg tttatcaggt gctccaggag    600
cacttgggca gggaatcgga tctcttcctg ctcgacagcc gtaccctctg ggcctcggag    660
gagggctggc tggtgtttga catcacagcc accagcaacc actgggtggt caatccgcgg    720
cacaacctgg gcctgcagct ctcggtggag acgctggatg ggcagagcat caaccccaag    780
ttggcgggcc tgattgggcg cacgggcccc cagaacaagc agcccttcat ggtggctttc    840
ttcaaggcca cggaggtcca cttccgcagc atccggtcca cggggagcaa acagagcagc    900
cagaaccgct ccaagacgcc caagaaccag gaagccctga gcatggccaa cgtggcagag    960
aacagcagca gcgaccagag gcaggcctgt aagaagcacg agctgtatgt cagcttccga   1020
gacctgggct ggcaggactg gatcatcgcg cctgaaggct acgccgccta ctactgtgag   1080
ggggagtgtg ccttccctct gaactcctac atgaacgcca ccaaccacgc catcgtgcag   1140
acgctggtcc acttcaggaa cccggaaacg gtgcccaagc cctgctgtgc gcccacgcag   1200
ctcaatgcca tctccgtcct ctacttcgat gacagctcca cgtcatcct gaagaaatac    1260
agaaacatgg tggtccgggc ctgtggctgc cac                                 1293
```

<210> SEQ ID NO 24
<211> LENGTH: 431
<212> TYPE: PRT
<213> ORGANISM: Artificial Sequence
<220> FEATURE:
<223> OTHER INFORMATION: hBMP-7 precursor derived variant peptide chain
      comprising the R299S, R314S, and I386R mutations
      and encoded by a Homo sapiens derived cDNA.

<400> SEQUENCE: 24

Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser

-continued

```
                35                  40                  45
Gln Glu Arg Arg Glu Met Gln Arg Glu Ile Leu Ser Ile Leu Gly Leu
 50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Lys Ala Thr Glu Val His Phe
            275                 280                 285

Arg Ser Ile Arg Ser Thr Gly Ser Lys Gln Ser Ser Gln Asn Arg Ser
290                 295                 300

Lys Thr Pro Lys Asn Gln Glu Ala Leu Ser Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
370                 375                 380

Phe Arg Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 25
<211> LENGTH: 1293
<212> TYPE: DNA
<213> ORGANISM: Artificial Sequence
```

<220> FEATURE:
<223> OTHER INFORMATION: Homo sapiens derived cDNA encoding a hBMP-7 precursor derived variant peptide chain comprising the R299S, R314S, and I386R mutations.

<400> SEQUENCE: 25

```
atgcacgtgc gctcactgcg agctgcggcg ccgcacagct tcgtggcgct ctgggcaccc        60
ctgttcctgc tgcgctccgc cctggccgac ttcagcctgg acaacgaggt gcactcgagc       120
ttcatccacc ggcgcctccg cagccaggag cggcgggaga tgcagcgcga gatcctctcc       180
attttgggct tgccccaccg cccgcgcccg cacctccagg gcaagcacaa ctcggcaccc       240
atgttcatgc tggacctgta caacgccatg gcggtggagg agggcggcgg gcccggcggc       300
cagggcttct cctacccta aaggccgtc ttcagtaccc agggccccc tctggccagc         360
ctgcaagata gccatttcct caccgacgcc gacatggtca tgagcttcgt caacctcgtg       420
gaacatgaca aggaattctt ccacccacgc taccaccatc gagagttccg gtttgatctt       480
tccaagatcc agaaggggga agctgtcacg gcagccgaat ccggatctca aaggactac        540
atccgggaac gcttcgacaa tgagacgttc cggatcagcg tttatcaggt gctccaggag       600
cacttgggca gggaatcgga tctcttcctg ctcgacagcc gtaccctctg gcctcggag        660
gagggctggc tggtgtttga catcacagcc accagcaacc actgggtggt caatccgcgg       720
cacaacctgg gcctgcagct ctcggtggag acgctggatg gcagagcat caaccccaag        780
ttggcgggcc tgattgggcg cacgggccc cagaacaagc agcccttcat ggtggctttc       840
ttcaaggcca cggaggtcca cttccgcagc atccggtcca cggggagcaa acagagcagc       900
cagaaccgct ccaagacgcc caagaaccag gaagccctga gcatggccaa cgtggcagag       960
aacagcagca cgcgaccagag gcaggcctgt aagaagcacg agctgtatgt cagcttccga      1020
gacctgggct ggcaggactg gatcatcgcg cctgaaggct acgccgccta ctactgtgag      1080
ggggagtgtg ccttcctct gaactcctac atgaacgcca ccaaccacgc catcgtgcag       1140
acgctggtcc acttcaacaa cccggaaacg gtgcccaagc cctgctgtgc gcccacgcag      1200
ctcaatgcca tctccgtcct ctacttcgat gacagctcca cgtcatcct gaagaaatac        1260
agaaacatgg tggtccgggc ctgtggctgc cac                                   1293
```

<210> SEQ ID NO 26
<211> LENGTH: 431
<212> TYPE: PRT
<213> ORGANISM: Artificial Sequence
<220> FEATURE:
<223> OTHER INFORMATION: hBMP-7 precursor derived variant peptide chain comprising the R299S, R314S, and I386R mutations and encoded by a Homo sapiens derived cDNA.

<400> SEQUENCE: 26

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly

-continued

```
                    85                  90                  95
Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Ser Ser Gln Asn Arg Ser
290                 295                 300

Lys Thr Pro Lys Asn Gln Glu Ala Leu Ser Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
370                 375                 380

Phe Asn Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430
```

<210> SEQ ID NO 27
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the R299S, R314S, V383K, L407K, and F409K
      mutations.

<400> SEQUENCE: 27
atgcacgtgc gctcactgcg agctgcggcg ccgcacagct tcgtggcgct ctgggcaccc    60

-continued

```
ctgttcctgc tgcgctccgc cctggccgac ttcagcctgg acaacgaggt gcactcgagc    120
ttcatccacc ggcgcctccg cagccaggag cggcgggaga tgcagcgcga gatcctctcc    180
attttgggct gccccaccg cccgcgcccg cacctccagg gcaagcacaa ctcggcaccc     240
atgttcatgc tggacctgta caacgccatg gcggtggagg agggcggcgg gcccggcggc    300
cagggcttct cctaccccta caaggccgtc ttcagtaccc agggcccccc tctggccagc    360
ctgcaagata gccatttcct caccgacgcc gacatggtca tgagcttcgt caacctcgtg    420
gaacatgaca aggaattctt ccacccacgc taccaccatc gagagttccg gtttgatctt    480
tccaagatcc agaagggga agctgtcacg gcagccgaat ccggatcta caaggactac     540 atccgggaac gcttcgacaa tgagacgttc cggatcagcg tttatcaggt gctccaggag    600
cacttgggca gggaatcgga tctcttcctg ctcgacagcc gtaccctctg gcctcggag    660 gagggctggc tggtgtttga catcacagcc accagcaacc actgggtggt caatccgcgg    720
cacaacctgg gcctgcagct ctcggtggag acgctggatg gcagagcat caaccccaag    780 ttggcgggcc tgattgggcg cacgggccc cagaacaagc agccttcat ggtggctttc      840 ttcaaggcca cggaggtcca cttccgcagc atccggtcca cggggagcaa acagagcagc    900
cagaaccgct ccaagacgcc caagaaccag gaagccctga gcatggccaa cgtggcagag    960
aacagcagca gcgaccagag gcaggcctgt aagaagcacg agctgtatgt cagcttccga   1020
gacctgggct ggcaggactg gatcatcgcg cctgaaggct acgccgccta ctactgtgag   1080
ggggagtgtg ccttccctct gaactcctac atgaacgcca ccaaccacgc catcgtgcag   1140
acgctgaagc acttcatcaa cccggaaacg gtgcccaagc cctgctgtgc gcccacgcag   1200
ctcaatgcca tctccgtcaa gtacaaggat gacagctcca cgtcatcct gaagaaatac     1260 agaaacatgg tggtccgggc ctgtggctgc cac                                1293
```

<210> SEQ ID NO 28
<211> LENGTH: 431
<212> TYPE: PRT
<213> ORGANISM: Artificial Sequence
<220> FEATURE:
<223> OTHER INFORMATION: hBMP-7 precursor derived variant peptide chain
comprising the R299S, R314S, V383K, L407K, and
F409K mutations and encoded by a Homo sapiens
derived cDNA.

<400> SEQUENCE: 28

```
Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125
```

Asp Ala Asp Met Val Met Ser Phe Val Asn Leu Val Glu His Asp Lys
     130                 135                 140
Glu Phe Phe His Pro Arg Tyr His Arg Glu Phe Arg Phe Asp Leu
145                 150                 155                 160
Ser Lys Ile Pro Glu Gly Glu Ala Val Thr Ala Ala Glu Phe Arg Ile
                165                 170                 175
Tyr Lys Asp Tyr Ile Arg Glu Arg Phe Asp Asn Glu Thr Phe Arg Ile
            180                 185                 190
Ser Val Tyr Gln Val Leu Gln Glu His Leu Gly Arg Glu Ser Asp Leu
        195                 200                 205
Phe Leu Leu Asp Ser Arg Thr Leu Trp Ala Ser Glu Glu Gly Trp Leu
210                 215                 220
Val Phe Asp Ile Thr Ala Thr Ser Asn His Trp Val Val Asn Pro Arg
225                 230                 235                 240
His Asn Leu Gly Leu Gln Leu Ser Val Glu Thr Leu Asp Gly Gln Ser
                245                 250                 255
Ile Asn Pro Lys Leu Ala Gly Leu Ile Gly Arg His Gly Pro Gln Asn
            260                 265                 270
Lys Gln Pro Phe Met Val Ala Phe Phe Lys Ala Thr Glu Val His Phe
        275                 280                 285
Arg Ser Ile Arg Ser Thr Gly Ser Lys Gln Ser Ser Asn Arg Ser
290                 295                 300
Lys Thr Pro Lys Asn Gln Glu Ala Leu Ser Met Ala Asn Val Ala Glu
305                 310                 315                 320
Asn Ser Ser Ser Asp Gln Arg Gln Ala Cys Lys Lys His Glu Leu Tyr
                325                 330                 335
Val Ser Phe Arg Asp Leu Gly Trp Gln Asp Trp Ile Ile Ala Pro Glu
            340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Lys His
370                 375                 380
Phe Ile Asn Pro Glu Thr Val Pro Lys Pro Cys Cys Ala Pro Thr Gln
385                 390                 395                 400
Leu Asn Ala Ile Ser Val Lys Tyr Lys Asp Asp Ser Ser Asn Val Ile
                405                 410                 415
Leu Lys Lys Tyr Arg Asn Met Val Val Arg Ala Cys Gly Cys His
            420                 425                 430

<210> SEQ ID NO 29
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the R299S, R314S, and W347D mutations.

<400> SEQUENCE: 29
atgcacgtgc gctcactgcg agctgcggcg ccgcacagct tcgtggcgct ctgggcaccc        60
ctgttcctgc tgcgctccgc cctggccgac ttcagcctgg acaacgaggt gcactcgagc       120
ttcatccacc ggcgcctccg cagccaggag cggcgggaga tgcagcgcga gatcctctcc       180
attttgggct tgccccaccg cccgcgcccg cacctccagg gcaagcacaa ctcggcaccc       240
atgttcatgc tggacctgta caacgccatg gcggtggagg agggcggcgg gcccggcggc       300

```
cagggcttct cctaccccta caaggccgtc ttcagtaccc agggcccccc tctggccagc    360
ctgcaagata gccatttcct caccgacgcc gacatggtca tgagcttcgt caacctcgtg    420
gaacatgaca aggaattctt ccacccacgc taccaccatc gagagttccg gtttgatctt    480
tccaagatcc cagaagggga agctgtcacg gcagccgaat ccggatctca aggactac     540 atccgggaac gcttcgacaa tgagacgttc cggatcagcg tttatcaggt gctccaggag    600
cacttgggca gggaatcgga tctcttcctg ctcgacagcc gtaccctctg gcctcggag     660 gagggctggc tggtgtttga catcacagcc accagcaacc actgggtggt caatccgcgg    720
cacaacctgg gcctgcagct ctcggtggag acgctggatg gcagagcat caaccccaag     780 ttggcgggcc tgattgggcg cacgggccc cagaacaagc agcccttcat ggtggctttc     840
ttcaaggcca cggaggtcca cttccgcagc atccggtcca cggggagcaa acagagcagc    900
cagaaccgct ccaagacgcc caagaaccag gaagccctga gcatggccaa cgtggcagag    960
aacagcagca gcgaccagag gcaggcctgt aagaagcacg agctgtatgt cagcttccga   1020
gacctgggct ggcaggacga catcatcgcg cctgaaggct acgccgccta ctactgtgag   1080
ggggagtgtg ccttccctct gaactcctac atgaacgcca ccaaccacgc catcgtgcag   1140
acgctggtcc acttcatcaa cccggaaacg gtgcccaagc cctgctgtgc gcccacgcag   1200
ctcaatgcca tctccgtcct ctacttcgat gacagctcca acgtcatcct gaagaaatac   1260
agaaacatgg tggtccgggc ctgtggctgc cac                                1293
```

<210> SEQ ID NO 30
<211> LENGTH: 431
<212> TYPE: PRT
<213> ORGANISM: Artificial Sequence
<220> FEATURE:
<223> OTHER INFORMATION: hBMP-7 precursor derived variant peptide chain
      comprising the R299S, R314S, and W347D mutations
      and encoded by a Homo sapiens derived cDNA.

<400> SEQUENCE: 30

```
Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
                 20                  25                  30

Leu Asp Asn Glu Val His Ser Ser Phe Ile His Arg Arg Leu Arg Ser
                 35                  40                  45

Gln Glu Arg Arg Glu Met Gln Arg Glu Ile Leu Ser Ile Leu Gly Leu
 50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
                115                 120                 125

Asp Ala Asp Met Val Met Ser Phe Val Asn Leu Val Glu His Asp Lys
                130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175
```

-continued

```
Tyr Lys Asp Tyr Ile Arg Glu Arg Phe Asp Asn Glu Thr Phe Arg Ile
                180                 185                 190
Ser Val Tyr Gln Val Leu Gln Glu His Leu Gly Arg Glu Ser Asp Leu
            195                 200                 205
Phe Leu Leu Asp Ser Arg Thr Leu Trp Ala Ser Glu Glu Gly Trp Leu
        210                 215                 220
Val Phe Asp Ile Thr Ala Thr Ser Asn His Trp Val Val Asn Pro Arg
225                 230                 235                 240
His Asn Leu Gly Leu Gln Leu Ser Val Glu Thr Leu Asp Gly Gln Ser
                245                 250                 255
Ile Asn Pro Lys Leu Ala Gly Leu Ile Gly Arg His Gly Pro Gln Asn
            260                 265                 270
Lys Gln Pro Phe Met Val Ala Phe Phe Lys Ala Thr Glu Val His Phe
        275                 280                 285
Arg Ser Ile Arg Ser Thr Gly Ser Lys Gln Ser Ser Gln Asn Arg Ser
        290                 295                 300
Lys Thr Pro Lys Asn Gln Glu Ala Leu Ser Met Ala Asn Val Ala Glu
305                 310                 315                 320
Asn Ser Ser Asp Gln Arg Gln Ala Cys Lys Lys His Glu Leu Tyr
                325                 330                 335
Val Ser Phe Arg Asp Leu Gly Trp Gln Asp Asp Ile Ile Ala Pro Glu
            340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Val His
        370                 375                 380
Phe Ile Asn Pro Glu Thr Val Pro Lys Pro Cys Cys Ala Pro Thr Gln
385                 390                 395                 400
Leu Asn Ala Ile Ser Val Leu Tyr Phe Asp Asp Ser Ser Asn Val Ile
                405                 410                 415
Leu Lys Lys Tyr Arg Asn Met Val Val Arg Ala Cys Gly Cys His
            420                 425                 430
```

<210> SEQ ID NO 31
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
  precursor derived variant peptide chain comprising
  the R299S, R314S, R421E, N422D, and R426E
  mutations.

<400> SEQUENCE: 31

```
atgcacgtgc gctcactgcg agctgcggcg ccgcacagct tcgtggcgct ctgggcaccc    60
ctgttcctgc tgcgctccgc cctggccgac ttcagcctgg acaacgaggt gcactcgagc   120
ttcatccacc ggcgcctccg cagccaggag cggcgggaga tgcagcgcga tcctctcc    180
attttgggct tgccccaccg cccgcgcccg cacctccagg caagcacaa ctcggcaccc    240
atgttcatgc tggacctgta caacgccatg gcggtggagg agggcggcgg gcccggcggc    300
cagggcttct cctaccccta caaggccgtc ttcagtaccc agggcccccc tctggccagc    360
ctgcaagata gccatttcct caccgacgcc gacatggtca tgagcttcgt caacctcgtg    420
gaacatgaca aggaattctt ccacccacgc taccaccatc gagagttccg gtttgatctt    480
tccaagatcc agaaggggga agctgtcacg gcagccgaat tccggatcta aaggactac    540
```

-continued

```
atccgggaac gcttcgacaa tgagacgttc cggatcagcg tttatcaggt gctccaggag    600
cacttgggca gggaatcgga tctcttcctg ctcgacagcc gtaccctctg ggcctcggag    660
gagggctggc tggtgtttga catcacagcc accagcaacc actgggtggt caatccgcgg    720
cacaacctgg gcctgcagct ctcggtggag acgctggatg ggcagagcat caaccccaag    780
ttggcgggcc tgattgggcg cacgggccc cagaacaagc agcccttcat ggtggctttc    840
ttcaaggcca cggaggtcca cttccgcagc atccggtcca cggggagcaa acagagcagc    900
cagaaccgct ccaagacgcc caagaaccag gaagccctga gcatggccaa cgtggcagag    960
aacagcagca gcgaccagag gcaggcctgt aagaagcacg agctgtatgt cagcttccga    1020
gacctgggct ggcaggactg gatcatcgcg cctgaaggct acgccgccta ctactgtgag    1080
ggggagtgtg ccttccctct gaactcctac atgaacgcca ccaaccacgc catcgtgcag    1140
acgctggtcc acttcatcaa cccggaaacg gtgcccaagc cctgctgtgc cccacgcag    1200 ctcaatgcca tctccgtcct ctacttcgat gacagctcca acgtcatcct gaagaaatac    1260
gaagacatgg tggtcgaggc ctgtggctgc cac                                1293
```

<210> SEQ ID NO 32
<211> LENGTH: 431
<212> TYPE: PRT
<213> ORGANISM: Artificial Sequence
<220> FEATURE:
<223> OTHER INFORMATION: hBMP-7 precursor derived variant peptide chain
      comprising the R299S, R314S, R421E, N422D, and
      R426E mutations and encoded by a Homo sapiens
      derived cDNA.

<400> SEQUENCE: 32

```
Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205
```

```
Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Lys Ala Thr Glu Val His Phe
            275                 280                 285

Arg Ser Ile Arg Ser Thr Gly Ser Lys Gln Ser Ser Gln Asn Arg Ser
    290                 295                 300

Lys Thr Pro Lys Asn Gln Glu Ala Leu Ser Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
                355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Glu Asp Met Val Val Glu Ala Cys Gly Cys His
            420                 425                 430

<210> SEQ ID NO 33
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the S293C, R299S, and R314S mutations.

<400> SEQUENCE: 33
atgcacgtgc gctcactgcg agctgcggcg ccgcacagct tcgtggcgct ctgggcaccc      60
ctgttcctgc tgcgctccgc cctggccgac ttcagcctgg acaacgaggt gcactcgagc     120
ttcatccacc ggcgcctccg cagccaggag cggcgggaga tgcagcgcga gatcctctcc     180
attttgggct gccccaccg cccgcgcccg cacctccagg gcaagcacaa ctcggcaccc     240
atgttcatgc tggacctgta caacgccatg gcggtggagg agggcggcgg gcccggcggc     300
cagggcttct cctacccta caaggccgtc ttcagtaccc agggccccc tctggccagc     360 ctgcaagata gccatttcct caccgacgcc gacatggtca tgagcttcgt caacctcgtg     420
gaacatgaca aggaattctt ccacccacgc taccaccatc gagagttccg gtttgatctt     480
tccaagatcc agaagggga agctgtcacg gcagccgaat ccggatcta aaggactac     540 atccgggaac gcttcgacaa tgagacgttc cggatcagcg tttatcaggt gctccaggag     600
cacttgggca gggaatcgga tctcttcctg ctcgacagcc gtaccctctg gcctcggag     660 gagggctggc tggtgtttga catcacagcc accagcaacc actgggtggt caatccgcgg     720
cacaacctgg gcctgcagct ctcggtggag acgctggatg ggcagagcat caaccccaag     780
```

-continued

```
ttggcgggcc tgattgggcg gcacgggccc cagaacaagc agcccttcat ggtggctttc      840
ttcaaggcca cggaggtcca cttccgcagc atccggtgca cggggagcaa acagagcagc      900
cagaaccgct ccaagacgcc caagaaccag gaagccctga gcatggccaa cgtggcagag      960
aacagcagca gcgaccagag gcaggcctgt aagaagcacg agctgtatgt cagcttccga     1020
gacctgggct ggcaggactg gatcatcgcg cctgaaggct acgccgccta ctactgtgag     1080
ggggagtgtg ccttccctct gaactcctac atgaacgcca ccaaccacgc catcgtgcag     1140
acgctggtcc acttcatcaa cccggaaacg gtgcccaagc cctgctgtgc gcccacgcag     1200
ctcaatgcca tctccgtcct ctacttcgat gacagctcca acgtcatcct gaagaaatac     1260
agaaacatgg tggtccgggc ctgtggctgc cac                                  1293
```

<210> SEQ ID NO 34
<211> LENGTH: 431
<212> TYPE: PRT
<213> ORGANISM: Artificial Sequence
<220> FEATURE:
<223> OTHER INFORMATION: hBMP-7 precursor derived variant peptide chain
      comprising the S293C, R299S, and R314S mutations
      and encoded by a Homo sapiens derived cDNA.

<400> SEQUENCE: 34

```
Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
           100                 105                 110

Thr Gln Gly Pro Pro Leu Ala Ser Leu Gln Asp Ser His Phe Leu Thr
       115                 120                 125

Asp Ala Asp Met Val Met Ser Phe Val Asn Leu Val Glu His Asp Lys
   130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255
```

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Cys Thr Gly Ser Lys Gln Ser Gln Asn Arg Ser
    290                 295                 300

Lys Thr Pro Lys Asn Gln Glu Ala Leu Ser Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 35
<211> LENGTH: 876
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the native hBMP-7 signal peptide and prodomain
      alone due to a deletion mutation that removed the
      hBMP-7 mature form domain.

<400> SEQUENCE: 35
atgcacgtgc gctcactgcg agctgcggcg ccgcacagct tcgtggcgct ctgggcaccc      60
ctgttcctgc tgcgctccgc cctggccgac ttcagcctgg acaacgaggt gcactcgagc     120
ttcatccacc ggcgcctccg cagccaggag cggcgggaga tgcagcgcga gatcctctcc     180
attttgggct gccccaccg cccgcgcccg cacctccagg gcaagcacaa ctcggcaccc     240
atgttcatgc tggacctgta caacgccatg gcggtggagg agggcggcgg gcccggcggc     300
cagggcttct cctaccccta caaggccgtc ttcagtaccc agggcccccc tctggccagc     360
ctgcaagata gccatttcct caccgacgcc gacatggtca tgagcttcgt caacctcgtg     420
gaacatgaca aggaattctt ccacccacgc taccaccatc gagagttccg gtttgatctt     480
tccaagatcc agaaggggga agctgtcacg gcagccgaat ccggatctta aggactac      540 atccgggaac gcttcgacaa tgagacgttc cggatcagcg tttatcaggt gctccaggag     600
cacttgggca gggaatcgga tctcttcctg ctcgacagcc gtaccctctg ggcctcggag     660
gagggctggc tggtgtttga catcacagcc accagcaacc actgggtggt caatccgcgg     720
cacaacctgg gcctgcagct ctcggtggag acgctggatg ggcagagcat caaccccaag     780
ttggcgggcc tgattgggcg gcacgggccc cagaacaagc agcccttcat ggtggctttc     840
ttcaaggcca cggaggtcca cttccgcagc atccgg                               876

<210> SEQ ID NO 36

```
<211> LENGTH: 292
<212> TYPE: PRT
<213> ORGANISM: Artificial Sequence
<220> FEATURE:
<223> OTHER INFORMATION: hBMP-7 precursor derived variant peptide chain
      comprising the native hBMP-7 signal peptide and
      prodomain alone due to a deletion mutation that
      removed the hBMP-7 mature form domain.  This
      hBMP-7 precursor derived variant peptide chain is
      encoded by a Homo sapiens derived cDNA.

<400> SEQUENCE: 36

Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg
    290

<210> SEQ ID NO 37
<211> LENGTH: 495
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the human growth hormone signal peptide instead of
``` the native hBMP-7 secretory signal peptide and the
    R299S and R314S mutations in the hBMP-7 mature
    form domain; the hBMP-7 prodomain has been removed
    by deletion mutation.

<400> SEQUENCE: 37

```
atggctacag gctcccggac gtccctgctc ctggcttttg gcctgctctg cctgccctgg    60
cttcaagagg gatccgcctc cacggggagc aaacagagca gccagaaccg ctccaagacg   120
cccaagaacc aggaagccct gagcatggcc aacgtggcag agaacagcag cagcgaccag   180
aggcaggcct gtaagaagca cgagctgtat gtcagcttcc gagacctggg ctggcaggac   240
tggatcatcg cgcctgaagg ctacgccgcc tactactgtg aggggagtg tgccttccct    300 ctgaactcct acatgaacgc caccaaccac gccatcgtgc agacgctggt ccacttcatc   360
aacccggaaa cggtgcccaa gccctgctgt gcgcccacgc agctcaatgc catctccgtc   420
ctctacttcg atgacagctc caacgtcatc ctgaagaaat acagaaacat ggtggtccgg   480
gcctgtggct gccac                                                    495
```

<210> SEQ ID NO 38
<211> LENGTH: 165
<212> TYPE: PRT
<213> ORGANISM: Artificial Sequence
<220> FEATURE:
<223> OTHER INFORMATION: hBMP-7 precursor derived variant peptide chain
    comprising the human growth hormone signal peptide
    instead of the native hBMP-7 secretory signal
    peptide and the R299S and R314S mutations in the
    hBMP-7 mature form domain; the hBMP-7 prodomain
    has been removed by deletion mutation. This
    hBMP-7 precursor derived variant peptide chain is
    encoded by a Homo sapiens derived cDNA.

<400> SEQUENCE: 38

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Ser Thr Gly Ser Lys Gln
            20                  25                  30

Ser Ser Gln Asn Arg Ser Lys Thr Pro Lys Asn Gln Glu Ala Leu Ser
        35                  40                  45

Met Ala Asn Val Ala Glu Asn Ser Ser Ser Asp Gln Arg Gln Ala Cys
    50                  55                  60

Lys Lys His Glu Leu Tyr Val Ser Phe Arg Asp Leu Gly Trp Gln Asp
65                  70                  75                  80

Trp Ile Ile Ala Pro Glu Gly Tyr Ala Ala Tyr Tyr Cys Glu Gly Glu
                85                  90                  95

Cys Ala Phe Pro Leu Asn Ser Tyr Met Asn Ala Thr Asn His Ala Ile
            100                 105                 110

Val Gln Thr Leu Val His Phe Ile Asn Pro Glu Thr Val Pro Lys Pro
        115                 120                 125

Cys Cys Ala Pro Thr Gln Leu Asn Ala Ile Ser Val Leu Tyr Phe Asp
    130                 135                 140

Asp Ser Ser Asn Val Ile Leu Lys Lys Tyr Arg Asn Met Val Val Arg
145                 150                 155                 160

Ala Cys Gly Cys His
                165
```

<210> SEQ ID NO 39
<211> LENGTH: 1263
<212> TYPE: DNA

<213> ORGANISM: Artificial Sequence
<220> FEATURE:
<223> OTHER INFORMATION: Homo sapiens derived cDNA encoding a hBMP-7
      precursor derived variant peptide chain comprising
      the Homo sapiens BMP-2 (hBMP-2) secretory signal
      peptide instead of the native hBMP-7 secretory
      signal peptide, the hBMP-2 prodomain instead of
      the native hBMP-7 prodomain, and the R299S and
      R314S mutations in the hBMP-7 mature form domain.

<400> SEQUENCE: 39

```
atggtggccg ggacccgctg tcttctagcg ttgctgcttc cccaggtcct cctgggcggc      60
gcggctggcc tcgttccgga gctgggccgc aggaagttcg cggcggcgtc gtcgggccgc     120
ccctcatccc agccctctga cgaggtcctg agcgagttcg agttgcggct gctcagcatg     180
ttcggcctga acagagacc cacccccagc agggacgccg tggtgccccc ctacatgcta     240
gacctgtatc gcaggcactc aggtcagccg ggctcacccg ccccagacca ccggttggag     300
agggcagcca gccgagccaa cactgtgcgc agcttccacc atgaagaatc tttggaagaa     360
ctaccagaaa cgagtgggaa acaacccgg agattcttct taatttaag ttctatcccc      420
acggaggagt ttatcacctc agcagagctt caggttttcc gagaacagat gcaagatgct     480
ttaggaaaca atagcagttt ccatcaccga attaatattt atgaaatcat aaaacctgca     540
acagccaact cgaaattccc cgtgaccaga cttttggaca ccaggttggt gaatcagaat     600
gcaagcaggt gggaaagttt tgatgtcacc cccgctgtga tgcggtggac tgcacaggga     660
cacgccaacc atggattcgt ggtggaagtg gcccacttgg aggagaaaca aggtgtctcc     720
aagagacatg ttaggataag caggtctttg caccaagatg aacacagctg gtcacagata     780
aggccattgc tagtaacttt tggccatgat ggaaaagggc atcctctcca caaaagagaa     840
aaaagatcta cggggagcaa acagagcagc cagaaccgct ccaagacgcc caagaaccag     900
gaagccctga gcatggccaa cgtggcagag aacagcagca cgaccagag caggcctgt      960
aagaagcacg agctgtatgt cagcttccga gacctgggct ggcaggactg gatcatcgcg    1020
cctgaaggct acgccgccta ctactgtgag ggggagtgtg ccttccctct gaactccctac   1080
atgaacgcca ccaaccacgc catcgtgcag acgctggtcc acttcatcaa cccggaaacg   1140
gtgcccaagc cctgctgtgc gcccacgcag ctcaatgcca tctccgtcct ctacttcgat   1200
gacagctcca acgtcatcct gaagaaatac agaaacatgg tggtccgggc ctgtggctgc   1260
cac                                                                  1263
```

<210> SEQ ID NO 40
<211> LENGTH: 421
<212> TYPE: PRT
<213> ORGANISM: Artificial Sequence
<220> FEATURE:
<223> OTHER INFORMATION: hBMP-7 precursor derived variant peptide chain
      comprising the Homo sapiens BMP-2 (hBMP-2)
      secretory signal peptide instead of the native
      hBMP-7 secretory signal peptide, the hBMP-2
      prodomain instead of the native hBMP-7 prodomain,
      and the R299S and R314S mutations in the hBMP-7
      mature form domain. This hBMP-7 precursor derived
      variant peptide chain is encoded by a Homo sapiens
      derived cDNA.

<400> SEQUENCE: 40

Met Val Ala Gly Thr Arg Cys Leu Leu Ala Leu Leu Leu Pro Gln Val
 1               5                  10                  15

Leu Leu Gly Gly Ala Ala Gly Leu Val Pro Glu Leu Gly Arg Arg Lys
            20                  25                  30

-continued

```
Phe Ala Ala Ser Ser Gly Arg Pro Ser Ser Gln Pro Ser Asp Glu
         35                  40                  45

Val Leu Ser Glu Phe Glu Leu Arg Leu Leu Ser Met Phe Gly Leu Lys
 50                  55                  60

Gln Arg Pro Thr Pro Ser Arg Asp Ala Val Val Pro Pro Tyr Met Leu
 65                  70                  75                  80

Asp Leu Tyr Arg Arg His Ser Gly Gln Pro Gly Ser Pro Ala Pro Asp
                 85                  90                  95

His Arg Leu Glu Arg Ala Ala Ser Arg Ala Asn Thr Val Arg Ser Phe
             100                 105                 110

His His Glu Glu Ser Leu Glu Glu Leu Pro Glu Thr Ser Gly Lys Thr
         115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                 165                 170                 175

Ile Lys Pro Ala Thr Ala Asn Ser Lys Phe Pro Val Thr Arg Leu Leu
             180                 185                 190

Asp Thr Arg Leu Val Asn Gln Asn Ala Ser Arg Trp Glu Ser Phe Asp
         195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                 245                 250                 255

Trp Ser Gln Ile Arg Pro Leu Leu Val Thr Phe Gly His Asp Gly Lys
             260                 265                 270

Gly His Pro Leu His Lys Arg Glu Lys Arg Ser Thr Gly Ser Lys Gln
         275                 280                 285

Ser Ser Gln Asn Arg Ser Lys Thr Pro Lys Asn Gln Glu Ala Leu Ser
290                 295                 300

Met Ala Asn Val Ala Glu Asn Ser Ser Ser Asp Gln Arg Gln Ala Cys
305                 310                 315                 320

Lys Lys His Glu Leu Tyr Val Ser Phe Arg Asp Leu Gly Trp Gln Asp
                 325                 330                 335

Trp Ile Ile Ala Pro Glu Gly Tyr Ala Ala Tyr Tyr Cys Glu Gly Glu
             340                 345                 350

Cys Ala Phe Pro Leu Asn Ser Tyr Met Asn Ala Thr Asn His Ala Ile
         355                 360                 365

Val Gln Thr Leu Val His Phe Ile Asn Pro Glu Thr Val Pro Lys Pro
370                 375                 380

Cys Cys Ala Pro Thr Gln Leu Asn Ala Ile Ser Val Leu Tyr Phe Asp
385                 390                 395                 400

Asp Ser Ser Asn Val Ile Leu Lys Lys Tyr Arg Asn Met Val Val Arg
                 405                 410                 415

Ala Cys Gly Cys His
             420

<210> SEQ ID NO 41
<211> LENGTH: 1293
```

<212> TYPE: DNA
<213> ORGANISM: Artificial Sequence
<220> FEATURE:
<223> OTHER INFORMATION: Homo sapiens derived cDNA encoding a hBMP-7
precursor derived variant peptide chain comprising
the H287R, R299S, R314S, R421E, N422D, and R426E
mutations.

<400> SEQUENCE: 41

| | | | |
|---|---|---|---|
| atgcacgtgc gctcactgcg agctgcggcg ccgcacagct tcgtggcgct ctgggcaccc | 60 |
| ctgttcctgc tgcgctccgc cctggccgac ttcagcctgg acaacgaggt gcactcgagc | 120 |
| ttcatccacc ggcgcctccg cagccaggag cggcgggaga tgcagcgcga gatcctctcc | 180 |
| attttgggct tgccccaccg cccgcgcccg cacctccagg gcaagcacaa ctcggcaccc | 240 |
| atgttcatgc tggacctgta caacgccatg gcggtggagg agggcggcgg gcccggcggc | 300 |
| cagggcttct cctacccocta caaggccgtc ttcagtaccc agggccccccc tctggccagc | 360 |
| ctgcaagata gccatttcct caccgacgcc gacatggtca tgagcttcgt caacctcgtg | 420 |
| gaacatgaca aggaattctt ccacccacgc taccaccatc gagagttccg gtttgatctt | 480 |
| tccaagatcc cagaagggga agctgtcacg gcagccgaat ccggatctca aggactac | 540 |
| atccgggaac gcttcgacaa tgagacgttc cggatcagcg tttatcaggt gctccaggag | 600 |
| cacttgggca gggaatcgga tctcttcctg ctcgacagcc gtaccctctg gcctcggag | 660 |
| gagggctggc tggtgtttga catcacagcc accagcaacc actgggtggt caatccgcgg | 720 |
| cacaacctgg gcctgcagct ctcggtggag acgctggatg ggcagagcat caaccccaag | 780 |
| ttggcgggcc tgattgggcg gcacgggccc cagaacaagc agcccttcat ggtggctttc | 840 |
| ttcaaggcca cggaggtccg cttccgcagc atccggtcca cgggggagcaa acagagcagc | 900 |
| cagaaccgct ccaagacgcc caagaaccag gaagccctga gcatggccaa cgtggcagag | 960 |
| aacagcagca cgcgaccaga gcaggcctgt aagaagcacg agctgtatgt cagcttccga | 1020 |
| gacctgggct ggcaggactg gatcatcgcg cctaaggct acgccgccta ctactgtgag | 1080 |
| ggggagtgtg ccttcccctct gaactcctac atgaacgcca ccaaccacgc catcgtgcag | 1140 |
| acgctggtcc acttcatcaa cccggaaacg gtgcccaagc cctgctgtgc gcccacgcag | 1200 |
| ctcaatgcca tctccgtcct ctacttcgat gacagctcca acgtcatcct gaagaaatac | 1260 |
| gaagacatgg tggtcgaggc ctgtggctgc cac | 1293 |

<210> SEQ ID NO 42
<211> LENGTH: 431
<212> TYPE: PRT
<213> ORGANISM: Artificial Sequence
<220> FEATURE:
<223> OTHER INFORMATION: hBMP-7 precursor derived variant peptide chain
comprising the H287R, R299S, R314S, R421E, N422D,
and R426E mutations and encoded by a Homo sapiens
derived cDNA.

<400> SEQUENCE: 42

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

-continued

```
Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val Arg Phe
        275                 280                 285

Arg Ser Ile Arg Ser Thr Gly Ser Lys Gln Ser Ser Gln Asn Arg Ser
290                 295                 300

Lys Thr Pro Lys Asn Gln Glu Ala Leu Ser Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Glu Asp Met Val Val Glu Ala Cys Gly Cys His
            420                 425                 430
```

<210> SEQ ID NO 43
<211> LENGTH: 1263
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the Homo sapiens BMP-2 (hBMP-2) secretory signal
      peptide instead of the native hBMP-7 secretory signal peptide, the hBMP-2 prodomain instead of
the native hBMP-7 prodomain, and the R299S, R314S,
R421E, N422D and R426E mutations in the hBMP-7
mature form domain.

<400> SEQUENCE: 43

| | | | | | |
|---|---|---|---|---|---|
| atggtggccg | ggacccgctg | tcttctagcg | ttgctgcttc | cccaggtcct | cctgggcggc | 60 |
| gcggctggcc | tcgttccgga | gctgggccgc | aggaagttcg | cggcggcgtc | gtcgggccgc | 120 |
| ccctcatccc | agccctctga | cgaggtcctg | agcgagttcg | agttgcggct | gctcagcatg | 180 |
| ttcggcctga | aacagagacc | cacccccagc | agggacgccg | tggtgccccc | ctacatgcta | 240 |
| gacctgtatc | gcaggcactc | aggtcagccg | ggctcacccg | ccccagacca | ccggttggag | 300 |
| agggcagcca | gccgagccaa | cactgtgcgc | agcttccacc | atgaagaatc | tttggaagaa | 360 |
| ctaccagaaa | cgagtgggaa | acaacccggg | agattcttct | ttaatttaag | ttctatcccc | 420 |
| acggaggagt | ttatcacctc | agcagagctt | caggttttcc | gagaacagat | gcaagatgct | 480 |
| ttaggaaaca | atagcagttt | ccatcaccga | attaatattt | atgaaatcat | aaaacctgca | 540 |
| acagccaact | cgaaattccc | cgtgaccaga | cttttggaca | ccaggttggt | gaatcagaat | 600 |
| gcaagcaggt | gggaaagttt | tgatgtcacc | cccgctgtga | tgcgtggac | tgcacaggga | 660 |
| cacgccaacc | atggattcgt | ggtggaagtg | gcccacttgg | aggagaaaca | aggtgtctcc | 720 |
| aagagacatg | ttaggataag | caggtctttg | caccaagatg | aacacagctg | gtcacagata | 780 |
| aggccattgc | tagtaacttt | tggccatgat | ggaaaagggc | atcctctcca | caaaagagaa | 840 |
| aaaagatcta | cggggagcaa | acagagcagc | cagaaccgct | ccaagacgcc | caagaaccag | 900 |
| gaagccctga | gcatggccaa | cgtggcagag | aacagcagca | gcgaccagag | gcaggcctgt | 960 |
| aagaagcacg | agctgtatgt | cagcttccga | gacctgggct | ggcaggactg | gatcatcgcg | 1020 |
| cctgaaggct | acgccgccta | ctactgtgag | ggggagtgtg | ccttccctct | gaactcctac | 1080 |
| atgaacgcca | ccaaccacgc | catcgtgcag | acgctggtcc | acttcatcaa | cccggaaacg | 1140 |
| gtgcccaagc | cctgctgtgc | gcccacgcag | ctcaatgcca | tctccgtcct | ctacttcgat | 1200 |
| gacagctcca | acgtcatcct | gaagaaatac | gaagacatgg | tggtcgaggc | ctgtggctgc | 1260 |
| cac | | | | | | 1263 |

<210> SEQ ID NO 44
<211> LENGTH: 421
<212> TYPE: PRT
<213> ORGANISM: Artificial Sequence
<220> FEATURE:
<223> OTHER INFORMATION: hBMP-7 precursor derived variant peptide chain
comprising the Homo sapiens BMP-2 (hBMP-2)
secretory signal peptide instead of the native
hBMP-7 secretory signal peptide, the hBMP-2
prodomain instead of the native hBMP-7 prodomain,
and the R299S, R314S, R421E, N422D and R426E
mutations in the hBMP-7 mature form domain. This
hBMP-7 precursor derived variant peptide chain is
encoded by a Homo sapiens derived cDNA.

<400> SEQUENCE: 44

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys

```
                50                  55                  60
Gln Arg Pro Thr Pro Ser Arg Asp Ala Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Leu Pro Glu Thr Ser Gly Lys Thr
            115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
            195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Ser Thr Gly Ser Lys Gln
            275                 280                 285

Ser Ser Gln Asn Arg Ser Lys Thr Pro Lys Asn Gln Glu Ala Leu Ser
290                 295                 300

Met Ala Asn Val Ala Glu Asn Ser Ser Ser Asp Gln Arg Gln Ala Cys
305                 310                 315                 320

Lys Lys His Glu Leu Tyr Val Ser Phe Arg Asp Leu Gly Trp Gln Asp
                325                 330                 335

Trp Ile Ile Ala Pro Glu Gly Tyr Ala Ala Tyr Tyr Cys Glu Gly Glu
            340                 345                 350

Cys Ala Phe Pro Leu Asn Ser Tyr Met Asn Ala Thr Asn His Ala Ile
            355                 360                 365

Val Gln Thr Leu Val His Phe Ile Asn Pro Glu Thr Val Pro Lys Pro
370                 375                 380

Cys Cys Ala Pro Thr Gln Leu Asn Ala Ile Ser Val Leu Tyr Phe Asp
385                 390                 395                 400

Asp Ser Ser Asn Val Ile Leu Lys Lys Tyr Glu Asp Met Val Val Glu
                405                 410                 415

Ala Cys Gly Cys His
            420

<210> SEQ ID NO 45
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
``` the H287T, R299S, and R314S mutations.

<400> SEQUENCE: 45

```
atgcacgtgc gctcactgcg agctgcggcg ccgcacagct tcgtggcgct ctgggcaccc      60
ctgttcctgc tgcgctccgc cctggccgac ttcagcctgg acaacgaggt gcactcgagc     120
ttcatccacc ggcgcctccg cagccaggag cggcgggaga tgcagcgcga gatcctctcc     180
attttgggct tgccccaccg cccgcgcccg cacctccagg gcaagcacaa ctcggcaccc     240
atgttcatgc tggacctgta caacgccatg gcggtggagg agggcggcgg gcccggcggc     300
cagggcttct cctaccccta caaggccgtc ttcagtaccc agggccccc tctggccagc     360
ctgcaagata gccatttcct caccgacgcc gacatggtca tgagcttcgt caacctcgtg     420
gaacatgaca aggaattctt ccacccacgc taccaccatc gagagttccg gtttgatctt     480
tccaagatcc agaaggggga agctgtcacg gcagccgaat ccggatctca aggactac      540
atccgggaac gcttcgacaa tgagacgttc cggatcagcg tttatcaggt gctccaggag     600
cacttgggca gggaatcgga tctcttcctg ctcgacagcc gtaccctctg gcctcggag      660
gagggctggc tggtgtttga catcacagcc accagcaacc actgggtggt caatccgcgg     720
cacaacctgg gcctgcagct ctcggtggag acgctggatg ggcagagcat caaccccaag     780
ttggcgggcc tgattgggcg cacgggccc agaacaagc agcccttcat ggtggctttc       840
ttcaaggcca cggaggtccg cttccgcagc atccggtcca cggggagcaa acagagcagc     900
cagaaccgct ccaagacgcc caagaaccag gaagccctga gcatggccaa cgtggcagag     960
aacagcagca gcgaccagag gcaggcctgt aagaagcacg agctgtatgt cagcttccga    1020
gacctgggct ggcaggactg gatcatcgcg cctgaaggct acgccgccta ctactgtgag    1080
ggggagtgtg ccttccctct gaactcctac atgaacgcca ccaaccacgc catcgtgcag    1140
acgctggtcc acttcatcaa cccggaaacg gtgcccaagc cctgctgtgc gcccacgcag    1200
ctcaatgcca tctccgtcct ctacttcgat gacagctcca acgtcatcct gaagaaatac    1260
agaaacatgg tggtccgggc ctgtggctgc cac                                 1293
```

<210> SEQ ID NO 46
<211> LENGTH: 431
<212> TYPE: PRT
<213> ORGANISM: Artificial Sequence
<220> FEATURE:
<223> OTHER INFORMATION: hBMP-7 precursor derived variant peptide chain comprising the H287T, R299S, and R314S mutations and encoded by a Homo sapiens derived cDNA.

<400> SEQUENCE: 46

```
Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
    65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
```

```
                100                 105                 110
Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
        180                 185                 190

Ser Val Tyr Gln Val Leu Gln Glu His Leu Gly Arg Glu Ser Asp Leu
    195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
        260                 265                 270

Lys Gln Pro Phe Met Val Ala Phe Phe Lys Ala Thr Glu Val Arg Phe
    275                 280                 285

Arg Ser Ile Arg Ser Thr Gly Ser Lys Gln Ser Ser Gln Asn Arg Ser
290                 295                 300

Lys Thr Pro Lys Asn Gln Glu Ala Leu Ser Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
        340                 345                 350

Gly Tyr Ala Ala Tyr Tyr Cys Glu Gly Glu Cys Ala Phe Pro Leu Asn
    355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
        420                 425                 430
```

<210> SEQ ID NO 47
<211> LENGTH: 1293
<212> TYPE: DNA
<213> ORGANISM: Artificial Sequence
<220> FEATURE:
<223> OTHER INFORMATION: Homo sapiens derived cDNA encoding a hBMP-7
      precursor derived variant peptide chain comprising
      the H287R, R299S, and R314S mutations.

<400> SEQUENCE: 47
atgcacgtgc gctcactgcg agctgcggcg ccgcacagct tcgtggcgct ctgggcaccc      60
ctgttcctgc tgcgctccgc cctggccgac tcagcctgg acaacgaggt gcactcgagc     120
ttcatccacc ggcgcctccg cagccaggag cggcgggaga tgcagcgcga gatcctctcc     180

```
attttgggct tgccccaccg cccgcgcccg cacctccagg gcaagcacaa ctcggcaccc    240
atgttcatgc tggacctgta caacgccatg gcggtggagg agggcggcgg gcccggcggc    300
cagggcttct cctaccccta caaggccgtc ttcagtaccc agggcccccc tctggccagc    360
ctgcaagata gccatttcct caccgacgcc gacatggtca tgagcttcgt caacctcgtg    420
gaacatgaca aggaattctt ccacccacgc taccaccatc gagagttccg gtttgatctt    480
tccaagatcc agaaggggga agctgtcacg gcagccgaat ccggatctca aggactac     540 atccgggaac gcttcgacaa tgagacgttc cggatcagcg tttatcaggt gctccaggag    600
cacttgggca gggaatcgga tctcttcctg ctcgacagcc gtaccctctg gcctcggag    660 gagggctggc tggtgtttga catcacagcc accagcaacc actgggtggt caatccgcgg    720
cacaacctgg gcctgcagct ctcggtggag acgctggatg gcagagcat caaccccaag     780 ttggcgggcc tgattgggcg cacgggccc agaacaagc agcccttcat ggtggctttc      840
ttcaaggcca cggaggtcac cttccgcagc atccggtcca cggggagcaa acagagcagc    900
cagaaccgct ccaagacgcc caagaaccag gaagccctga gcatggccaa cgtggcagag    960
aacagcagca gcgaccagag gcaggcctgt aagaagcacg agctgtatgt cagcttccga   1020
gacctgggct ggcaggactg gatcatcgcg cctgaaggct acgccgccta ctactgtgag    1080
ggggagtgtg ccttccctct gaactcctac atgaacgcca ccaaccacgc catcgtgcag    1140
acgctggtcc acttcatcaa cccggaaacg gtgcccaagc cctgctgtgc gcccacgcag   1200
ctcaatgcca tctccgtcct ctacttcgat gacagctcca acgtcatcct gaagaaatac   1260
agaaacatgg tggtccgggc ctgtggctgc cac                                1293
```

<210> SEQ ID NO 48
<211> LENGTH: 431
<212> TYPE: PRT
<213> ORGANISM: Artificial Sequence
<220> FEATURE:
<223> OTHER INFORMATION: hBMP-7 precursor derived variant peptide chain
      comprising the H287R, R299S, and R314S mutations
      and encoded by a Homo sapiens derived cDNA.

<400> SEQUENCE: 48

```
Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
```

-continued

```
              145                 150                 155                 160
     Ser Lys Ile Pro Glu Gly Glu Ala Val Thr Ala Ala Glu Phe Arg Ile
                     165                 170                 175

Tyr Lys Asp Tyr Ile Arg Glu Arg Phe Asp Asn Glu Thr Phe Arg Ile
                     180                 185                 190

Ser Val Tyr Gln Val Leu Gln Glu His Leu Gly Arg Glu Ser Asp Leu
                     195                 200                 205

Phe Leu Leu Asp Ser Arg Thr Leu Trp Ala Ser Glu Glu Gly Trp Leu
                     210                 215                 220

Val Phe Asp Ile Thr Ala Thr Ser Asn His Trp Val Val Asn Pro Arg
     225                 230                 235                 240

His Asn Leu Gly Leu Gln Leu Ser Val Glu Thr Leu Asp Gly Gln Ser
                     245                 250                 255

Ile Asn Pro Lys Leu Ala Gly Leu Ile Gly Arg His Gly Pro Gln Asn
                     260                 265                 270

Lys Gln Pro Phe Met Val Ala Phe Phe Lys Ala Thr Glu Val Thr Phe
                     275                 280                 285

Arg Ser Ile Arg Ser Thr Gly Ser Lys Gln Ser Ser Gln Asn Arg Ser
                     290                 295                 300

Lys Thr Pro Lys Asn Gln Glu Ala Leu Ser Met Ala Asn Val Ala Glu
     305                 310                 315                 320

Asn Ser Ser Ser Asp Gln Arg Gln Ala Cys Lys Lys His Glu Leu Tyr
                     325                 330                 335

Val Ser Phe Arg Asp Leu Gly Trp Gln Asp Trp Ile Ile Ala Pro Glu
                     340                 345                 350

Gly Tyr Ala Ala Tyr Tyr Cys Glu Gly Glu Cys Ala Phe Pro Leu Asn
                     355                 360                 365

Ser Tyr Met Asn Ala Thr Asn His Ala Ile Val Gln Thr Leu Val His
                     370                 375                 380

Phe Ile Asn Pro Glu Thr Val Pro Lys Pro Cys Cys Ala Pro Thr Gln
     385                 390                 395                 400

Leu Asn Ala Ile Ser Val Leu Tyr Phe Asp Asp Ser Ser Asn Val Ile
                     405                 410                 415

Leu Lys Lys Tyr Arg Asn Met Val Val Arg Ala Cys Gly Cys His
                     420                 425                 430
```

The invention claimed is:

1. An isolated peptide chain comprising the amino acid sequence shown in SEQ ID NO: 42.

2. A method of inducing osteogenesis comprising contacting bone cells with the peptide chain of claim 1.

3. A method of inducing kidney cell proliferation comprising contacting kidney cells with the peptide chain of claim 1.

* * * * *